US008506544B2

(12) United States Patent
Ashton et al.

(10) Patent No.: US 8,506,544 B2
(45) Date of Patent: Aug. 13, 2013

(54) DISPOSABLE ABSORBENT PANT WITH EFFICIENT DESIGN AND CONVENIENT SINGLE-SECTION SIDE STRETCH PANELS

(75) Inventors: Gregory Ashton, Cincinnati, OH (US); Masaharu Nishikawa, Cincinnati, OH (US); Michael Dale Trennepohl, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 291 days.

(21) Appl. No.: 12/819,473

(22) Filed: Jun. 21, 2010

(65) Prior Publication Data

US 2011/0313387 A1  Dec. 22, 2011

(51) Int. Cl.
*A61F 13/15* (2006.01)

(52) U.S. Cl.
USPC ............ 604/385.24; 604/385.26; 604/385.27; 604/385.28; 604/385.29

(58) Field of Classification Search
USPC ............. 604/385.24, 385.26, 385.27, 385.28, 604/385.29
See application file for complete search history.

(56) References Cited

U.S. PATENT DOCUMENTS

| | | |
|---|---|---|
| 2,344,375 A | 3/1944 | Stephens |
| 2,854,979 A | 10/1958 | Turner et al. |
| 4,938,753 A | 7/1990 | Van Gompel et al. |
| 4,938,757 A | 7/1990 | Van Gompel et al. |
| 4,940,464 A | 7/1990 | Van Gompel et al. |
| 5,143,679 A | 9/1992 | Weber et al. |
| 5,156,793 A | 10/1992 | Buell et al. |
| 5,167,897 A | 12/1992 | Weber et al. |
| 5,358,500 A | 10/1994 | Lavon et al. |
| 5,368,584 A | 11/1994 | Clear et al. |
| 5,370,634 A | 12/1994 | Ando et al. |
| 5,383,871 A | 1/1995 | Carlin et al. |
| 5,447,508 A | 9/1995 | Numano et al. |
| 5,531,729 A | 7/1996 | Coles et al. |
| 5,531,732 A | 7/1996 | Wood |
| 5,545,158 A | 8/1996 | Jessup |
| 5,554,144 A | 9/1996 | Roe et al. |
| 5,554,145 A | 9/1996 | Roe et al. |
| 5,569,232 A | 10/1996 | Roe et al. |
| 5,569,234 A | 10/1996 | Buell et al. |

(Continued)

FOREIGN PATENT DOCUMENTS

| | | |
|---|---|---|
| WO | WO-0265961 B1 | 2/2003 |
| WO | WO-2007141749 A1 | 2/2007 |

OTHER PUBLICATIONS

International Search Report mailed Sep. 30, 2011.
PCT International Search Report, dated Dec. 9, 2011 (19 pages).

*Primary Examiner* — Jacqueline F. Stephens
(74) *Attorney, Agent, or Firm* — William E. Gallagher

(57) ABSTRACT

A disposable absorbent pant having single-section side stretch panels is disclosed. The pant may have features including a seam with an overlapping configuration, and a seam with a sandwiched configuration. A seam of overlapping configuration may be formed by mechanical bonds that provide for tensile strength in a lateral direction, while providing tearability for convenient removal, and may include additional features that include indicia of a location of tearability, a tear-inducing notch, and structure to grasp for tearing. A seam of sandwiched configuration may be configured to provide a finished outward appearance and configured to provide extended lateral width of side stretch panels, providing for increased stretch, without extending overall hoop circumference of the pant, at risk of an undesirably loose fit. The pant may include other features that reduce usage of materials, including complementary cut side panels.

16 Claims, 20 Drawing Sheets

(56) References Cited

U.S. PATENT DOCUMENTS

| | | |
|---|---|---|
| 5,580,411 A | 12/1996 | Nease et al. |
| 5,591,155 A | 1/1997 | Nishikawa et al. |
| 5,624,420 A | 4/1997 | Bridges et al. |
| 5,669,897 A | 9/1997 | Lavon et al. |
| 5,685,874 A | 11/1997 | Buell et al. |
| 5,705,013 A | 1/1998 | Nease et al. |
| 5,807,368 A | 9/1998 | Helmer |
| 5,836,932 A | 11/1998 | Buell et al. |
| 5,843,068 A | 12/1998 | Allen et al. |
| 5,858,012 A | 1/1999 | Yamaki et al. |
| 5,876,391 A | 3/1999 | Roe et al. |
| 5,899,895 A | 5/1999 | Robles et al. |
| 5,904,673 A | 5/1999 | Roe et al. |
| 5,947,948 A | 9/1999 | Roe et al. |
| 5,957,908 A | 9/1999 | Kline et al. |
| 5,997,521 A | 12/1999 | Robles et al. |
| 6,004,306 A | 12/1999 | Robles et al. |
| 6,027,484 A | 2/2000 | Romare |
| 6,042,673 A | 3/2000 | Johnson et al. |
| 6,120,487 A | 9/2000 | Ashton |
| 6,120,489 A | 9/2000 | Johnson et al. |
| 6,258,077 B1 | 7/2001 | Buell et al. |
| 6,264,639 B1 | 7/2001 | Sauer |
| 6,297,424 B1 | 10/2001 | Olson et al. |
| 6,307,119 B1 | 10/2001 | Cammarota et al. |
| 6,308,339 B1 | 10/2001 | Murakami et al. |
| 6,325,787 B1 | 12/2001 | Roe et al. |
| 6,336,922 B1 | 1/2002 | Vangompel et al. |
| 6,352,528 B1 | 3/2002 | Weber et al. |
| 6,352,607 B1 | 3/2002 | Kuen et al. |
| 6,364,863 B1 | 4/2002 | Yamamoto et al. |
| 6,375,646 B1 | 4/2002 | Widlund et al. |
| 6,395,115 B1 | 5/2002 | Popp et al. |
| 6,443,940 B1 | 9/2002 | Ashton et al. |
| 6,478,785 B1 | 11/2002 | Ashton et al. |
| 6,494,873 B2 | 12/2002 | Karlsson et al. |
| 6,524,293 B1 | 2/2003 | Elsberg et al. |
| 6,551,294 B1 | 4/2003 | Elsberg et al. |
| 6,554,816 B1 | 4/2003 | Olson |
| 6,572,595 B1 | 6/2003 | Klemp et al. |
| 6,572,596 B2 | 6/2003 | Pargass et al. |
| 6,572,601 B2 | 6/2003 | Suprise et al. |
| 6,579,275 B1 | 6/2003 | Pozniak et al. |
| 6,626,879 B1 | 9/2003 | Ashton et al. |
| 6,635,041 B1 | 10/2003 | Popp et al. |
| 6,635,135 B2 | 10/2003 | Kuen et al. |
| 6,654,190 B2 | 11/2003 | Nath et al. |
| 6,669,678 B2 | 12/2003 | Hermansson et al. |
| 6,723,035 B2 | 4/2004 | Franklin et al. |
| 6,726,669 B2 | 4/2004 | Shimada et al. |
| 6,726,670 B2 | 4/2004 | Almberg et al. |
| 6,752,796 B2 | 6/2004 | Karami |
| 6,755,808 B2 | 6/2004 | Balogh et al. |
| 6,761,711 B1 | 7/2004 | Fletcher et al. |
| 6,780,173 B2 | 8/2004 | Mishima et al. |
| 6,817,994 B2 | 11/2004 | Popp et al. |
| 6,821,271 B2 | 11/2004 | Shinohara et al. |
| 6,830,566 B2 | 12/2004 | Kuen et al. |
| 6,837,879 B2 | 1/2005 | Kuen et al. |
| 6,840,930 B1 | 1/2005 | Miyamoto et al. |
| 6,843,872 B2 | 1/2005 | Morman |
| 6,846,374 B2 | 1/2005 | Popp et al. |
| 6,849,067 B2 | 2/2005 | Fletcher et al. |
| 6,863,666 B2 | 3/2005 | Minato |
| 6,869,424 B1 | 3/2005 | Morman et al. |
| 6,872,267 B2 | 3/2005 | Popp et al. |
| 6,902,796 B2 | 6/2005 | Morell et al. |
| 6,905,488 B2 | 6/2005 | Olson |
| 6,923,797 B2 | 8/2005 | Shinohara et al. |
| 6,926,702 B1 | 8/2005 | Wilkinson |
| 6,939,335 B2 | 9/2005 | Franke et al. |
| 6,949,089 B2 | 9/2005 | Olson et al. |
| 6,953,452 B2 | 10/2005 | Popp et al. |
| 6,955,668 B2 | 10/2005 | Almberg et al. |
| 6,976,978 B2 | 12/2005 | Ruman et al. |
| 6,978,486 B2 | 12/2005 | Zhou et al. |
| 6,981,968 B2 | 1/2006 | Kusibojoska et al. |
| 6,994,761 B2 | 2/2006 | Klemp et al. |
| 7,008,410 B2 | 3/2006 | Gustin et al. |
| 7,011,653 B2 | 3/2006 | Imsangjan et al. |
| 7,039,997 B2 | 5/2006 | Vogt et al. |
| 7,056,411 B2 | 6/2006 | Desai et al. |
| 7,074,215 B2 | 7/2006 | Ashton et al. |
| 7,077,834 B2 | 7/2006 | Bishop et al. |
| 7,101,360 B2 | 9/2006 | Sorenson et al. |
| 7,118,558 B2 | 10/2006 | Wu et al. |
| 7,153,833 B2 | 12/2006 | Rougeot et al. |
| 7,156,829 B2 | 1/2007 | Minato et al. |
| 7,162,749 B2 | 1/2007 | Carbone, II et al. |
| 7,172,585 B2 | 2/2007 | Sandin et al. |
| 7,201,744 B2 | 4/2007 | Van Gompel et al. |
| 7,217,260 B2 | 5/2007 | Molander et al. |
| 7,255,688 B2 | 8/2007 | Sasaki et al. |
| 7,288,079 B2 | 10/2007 | Toyoshima et al. |
| 7,294,593 B2 | 11/2007 | Morman et al. |
| 7,322,967 B2 | 1/2008 | Kondo |
| 7,331,946 B2 | 2/2008 | Shimada et al. |
| 7,404,813 B2 | 7/2008 | Van Gompel et al. |
| 7,432,413 B2 | 10/2008 | Roe et al. |
| 7,459,050 B2 | 12/2008 | Karlsson et al. |
| 7,462,172 B2 | 12/2008 | Wright et al. |
| 7,481,802 B2 | 1/2009 | Hermansson |
| 7,498,478 B2 | 3/2009 | Long et al. |
| 7,503,912 B2 | 3/2009 | Otsubo et al. |
| 7,520,873 B2 | 4/2009 | Sosalla et al. |
| 7,524,313 B2 | 4/2009 | Kline et al. |
| 7,534,237 B2 | 5/2009 | Olson et al. |
| 7,569,039 B2 | 8/2009 | Matsuda et al. |
| 7,572,248 B2 | 8/2009 | Ashton et al. |
| 7,578,812 B2 | 8/2009 | Datta et al. |
| 7,591,811 B2 | 9/2009 | Crislip Wilkinson |
| 7,608,068 B2 | 10/2009 | Fujioka |
| 7,615,040 B2 | 11/2009 | Olson et al. |
| 7,641,641 B2 | 1/2010 | Ramshak |
| 7,642,398 B2 | 1/2010 | Järpenberg et al. |
| 7,695,464 B2 | 4/2010 | Fletcher et al. |
| 7,722,592 B2 | 5/2010 | Dalal et al. |
| 7,754,939 B2 | 7/2010 | Yoshida et al. |
| 7,758,559 B2 | 7/2010 | Sugito |
| 7,765,614 B2 | 8/2010 | Takino et al. |
| 7,799,007 B2 | 9/2010 | Hermansson et al. |
| 7,806,880 B2 | 10/2010 | Roe et al. |
| 7,807,861 B2 | 10/2010 | Molander et al. |
| 7,850,670 B2 | 12/2010 | Reyes |
| 7,963,953 B2 | 6/2011 | Erdman et al. |
| 2001/0041879 A1 | 11/2001 | Karami et al. |
| 2002/0042600 A1 | 4/2002 | Datta et al. |
| 2002/0111596 A1 | 8/2002 | Fletcher et al. |
| 2002/0123730 A1 | 9/2002 | Popp et al. |
| 2002/0138065 A1 | 9/2002 | Yeater et al. |
| 2002/0151858 A1 | 10/2002 | Karami et al. |
| 2002/0165518 A1 | 11/2002 | Datta et al. |
| 2003/0018316 A1 | 1/2003 | Kusibojoska et al. |
| 2003/0069557 A1 | 4/2003 | Driskell et al. |
| 2003/0083634 A1 | 5/2003 | Fernfors |
| 2003/0088220 A1 | 5/2003 | Molander et al. |
| 2003/0091807 A1 | 5/2003 | Desai et al. |
| 2003/0109842 A1 | 6/2003 | Louis et al. |
| 2003/0153889 A1 | 8/2003 | Gibbs |
| 2003/0181883 A1 | 9/2003 | Olson et al. |
| 2003/0212378 A1 | 11/2003 | Kuen et al. |
| 2004/0002691 A1 | 1/2004 | Popp et al. |
| 2004/0030318 A1 | 2/2004 | Karlsson et al. |
| 2004/0127876 A1 | 7/2004 | Stevens |
| 2004/0127881 A1 | 7/2004 | Stevens et al. |
| 2004/0222553 A1 | 11/2004 | Desai et al. |
| 2004/0243083 A1 | 12/2004 | Matsuda et al. |
| 2004/0254550 A1 | 12/2004 | Huang et al. |
| 2005/0059947 A1 | 3/2005 | Murguly |
| 2005/0059950 A1 | 3/2005 | Murguly |
| 2005/0113791 A1 | 5/2005 | Neubauer et al. |
| 2006/0004339 A1 | 1/2006 | Lord et al. |
| 2006/0069376 A1 | 3/2006 | Miller et al. |
| 2006/0167434 A1 | 7/2006 | Ashton et al. |

| | | |
|---|---|---|
| 2006/0173435 A1 | 8/2006 | Nakajima et al. |
| 2006/0178651 A1 | 8/2006 | Glaug |
| 2006/0212010 A1 | 9/2006 | Roe et al. |
| 2006/0241560 A1 | 10/2006 | Chang et al. |
| 2006/0271009 A1 | 11/2006 | Cartier et al. |
| 2007/0016155 A1 | 1/2007 | Chang et al. |
| 2007/0032766 A1 | 2/2007 | Liu et al. |
| 2007/0073261 A1 | 3/2007 | Ashton et al. |
| 2007/0088309 A1 | 4/2007 | Ehrnsperger et al. |
| 2007/0142808 A1 | 6/2007 | Wada et al. |
| 2007/0249254 A1 | 10/2007 | Mansfield |
| 2007/0255246 A1 | 11/2007 | Schneider |
| 2007/0287975 A1 | 12/2007 | Fujimoto et al. |
| 2007/0287980 A1 | 12/2007 | Kline et al. |
| 2007/0293111 A1 | 12/2007 | Mansfield |
| 2008/0027406 A1 | 1/2008 | Shirai et al. |
| 2008/0276352 A1 | 11/2008 | Strange et al. |
| 2008/0294137 A1 | 11/2008 | Jansson |
| 2009/0036860 A1 | 2/2009 | Sugiyama et al. |
| 2009/0043272 A1 | 2/2009 | Jackson et al. |
| 2009/0043275 A1 | 2/2009 | Perneborn |
| 2009/0048572 A1 | 2/2009 | Karlsson et al. |
| 2009/0069772 A1 | 3/2009 | Sauer et al. |
| 2009/0069773 A1 | 3/2009 | Sauer et al. |
| 2009/0069774 A1 | 3/2009 | Sauer et al. |
| 2009/0069775 A1 | 3/2009 | Sauer et al. |
| 2009/0069777 A1 | 3/2009 | Sauer et al. |
| 2009/0069778 A1 | 3/2009 | Sauer et al. |
| 2009/0069779 A1 | 3/2009 | Sauer et al. |
| 2009/0069781 A1 | 3/2009 | Sauer et al. |
| 2009/0069782 A1 | 3/2009 | Sauer et al. |
| 2009/0077720 A1 | 3/2009 | Shinomiya |
| 2009/0157034 A1 | 6/2009 | Mattingly et al. |

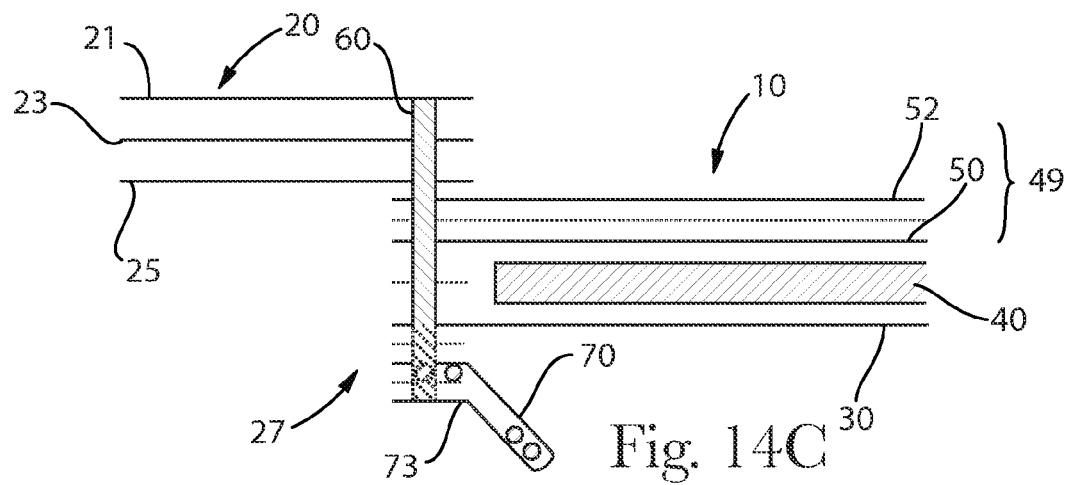
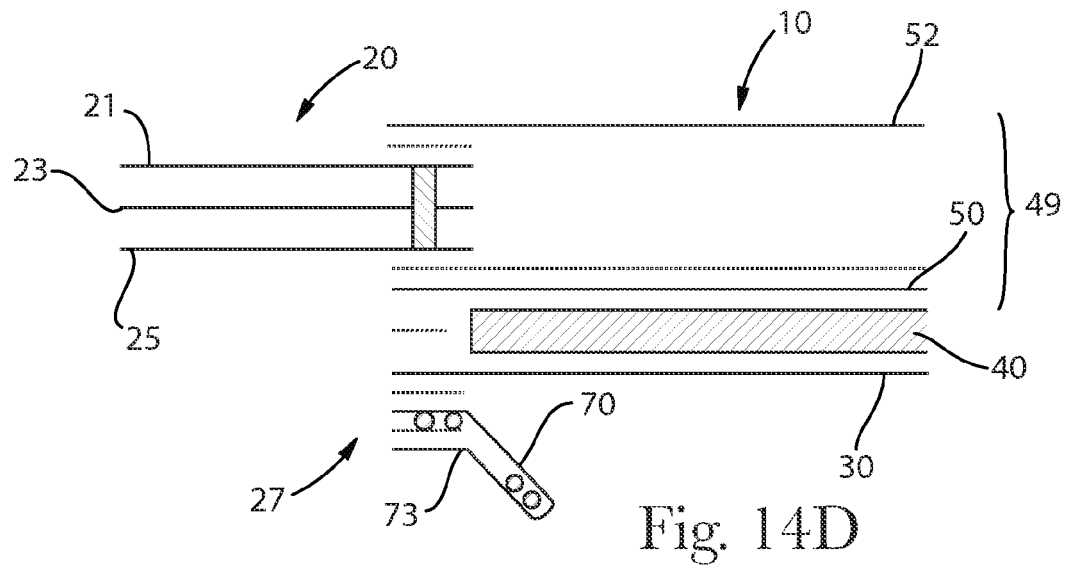

DISPOSABLE ABSORBENT PANT WITH EFFICIENT DESIGN AND CONVENIENT SINGLE-SECTION SIDE STRETCH PANELS

BACKGROUND OF THE IN

Disposable absorbent diapers configured to be donned like pants, in that to be donned they are pulled on over the wearer's feet and up the legs rather than wrapped directly about and fastened at the wearer's lower torso like an infant diaper, have been in the market for a number of years. Such products are often marketed as "training pants" intended for children who are walking, beginning to develop independence and dress themselves, and learning to control their bodily functions so that they can transition out of diapers and into underwear. Such training pants provide a toilet-training child with an underwear-like garment that she can learn to don herself in the same manner as underpants, providing a new sense of accomplishment and independence, while still providing protection against accidents.

Similar articles are marketed in larger sizes and intended for older children experiencing childhood enuresis, or adults experiencing incontinence.

Currently marketed designs are constructed from a rectangular or hourglass-shaped precursor chassis having a liquid impermeable, garment-facing backsheet, liquid permeable, wearer-facing topsheet and an absorbent core between the backsheet and the topsheet. The chassis of the typical design will have front and rear waist regions and a crotch region between the waist regions, and respective front and rear pairs of stretch panels formed of a laterally, elastically stretchable and contractible stretch laminate, extending from each of the waist regions, with the respective front and rear panels on each side then joined together at side seams to form a pant-like structure. The stretch laminate panels at the sides provide for elastic hoop-wise expansion of the article to allow it to be pulled over body contours while being donned, and elastic hoop-wise contraction to hold the article comfortably and securely in place while being worn.

While sufficiently popular to sustain their presence in the market, current designs present at least several challenges.

Because such products are "disposable" for the consumer and the industry is highly competitive (factors that exert downward pressure on pricing), the business of manufacturing disposable absorbent pants requires large scale and production volume for success. Thus, in addition to product quality, performance, fit, appearance and consumer satisfaction, cost and material conservation are an ever-present and ever-important objective. Elastomeric materials used as components of stretch laminates are among the more expensive components of many current disposable absorbent pant designs. Consequently, inclusion of such materials to any extent that is unnecessary to provide their intended function (elastic stretch and contraction) is undesirable.

The amount of overall lateral hoop-wise expansion available in a disposable absorbent pant is affected by the lateral width of the stretch panels (i.e., the greater the lateral width of the stretch panel, the greater the amount of lateral expansion that it will provide). Thus, the respective front and rear stretch panels must be of a sufficient lateral width to provide for the amount of lateral hoop stretch required for the intended wearer to easily and comfortably don the pant. Generally, increasing stretch capability by increasing the lateral width of the stretch panels provides for easier and more comfortable donning. On the other hand, once the pant is donned and in wearing position on the wearer, contraction is required to provide a secure, neat fit and exudate containment functionality. If the stretch panels are excessively wide, they will not be stretched enough in wearing position to provide sufficient contractive securing tension, and an unacceptably loose/sloppy fit can be the result. Generally, decreasing the lateral width of the stretch panels increases the snugness, neatness and security of the fit and containment functionality. Thus, in designing stretch panels and selecting their width, competing and conflicting objectives are presented.

Further, the precursor from and rear stretch panels must have additional lateral width available to form the seams along which they are to be attached. The seams typically include a section of the stretch laminate that is relatively fixed, such that it cannot serve to provide stretch capability. Thus, in one sense, the stretch capability of the portions of the stretch laminate material (including the relatively expensive elastomeric materials) required for side seams is wasted. Considering the production volumes required for competitiveness in the market, this is not an insignificant factor.

Additionally, the typical chassis, and especially the liquid impermeable backsheet thereof, will be required to be of a certain lateral width at the front and rear waist regions in order to provide desired containment of urine or other liquid exudates, and a desired width of the envelope structure containing the absorbent core. The needed lateral width of the backsheet will take up substantial portions of the lateral waist circumference. This leaves only a smaller fraction of the overall waist band length (at the side-hip areas available for stretch panels. In order to provide the stretch capability needed to strike the balance between the need for ease of donning and a secure fit, relatively high-performance elastomeric material is needed for the stretch laminate—which is relatively expensive. Some designs have added elastically stretchable members and suitable accompanying construction to the rear and/or front waist regions to supplement waistband stretch capability. This approach, however, adds its own cost and complexity to the design.

Further, it is often desirable for a training pant to be quickly and easily removable (such as when soiled with exudates), without the necessity of having to pull the article down over the wearer's legs and feet. For this reason, it may be desirable that portions of the pant are easily separable by the caregiver or wearer at one or more defined locations, so that it can be conveniently and neatly removed. One currently available design addresses this need by providing side seams held together only by strips of hook-type fastener components engaged with a compatible receiving material, which will allow relatively easy separation along the side seam when the caregiver or wearer applies requisite separating forces across the seam. However, this approach does not help with materials savings and in some circumstances may add cost and complexity to the design. Other design approaches have employed side seams in which the respective front and rear stretch panels are permanently bonded together. Although such approaches decrease the possibility of unintended separation, they also reduce the ease of removal.

In view of the foregoing, the design needs, and costs of materials typically used to make disposable absorbent pants, a need exists for improvements that will conserve materials and improve lateral hoop-wise stretch performance and wearer/caregiver convenience.

BRIEF DESCRIPTION OF THE DRAWINGS

Like components and/or features are given like numeric references throughout the drawings and views. In the drawings:

FIG. 14C is a schematic, exploded, lateral cross-sectional view of a seam having an overlapping configuration, and portions of a chassis and side panel at the seam arranged in one configuration, and also depicting a barrier cuff in one configuration attached at the seam, longitudinally below a location at which such cuff would be have its free edge tacked/bonded down;

FIG. 14D is a schematic, exploded, lateral cross-sectional view of a seam having a sandwiched configuration, and portions of a chassis and side panel at the seam arranged in an alternative configuration, and also depicting a barrier cuff in an alternative configuration attached at the seam, longitudinally below a location at which such cuff would be have its free edge tacked/bonded down;

DETAILED DESCRIPTION OF THE INVENTION

Definitions

Figure 1:
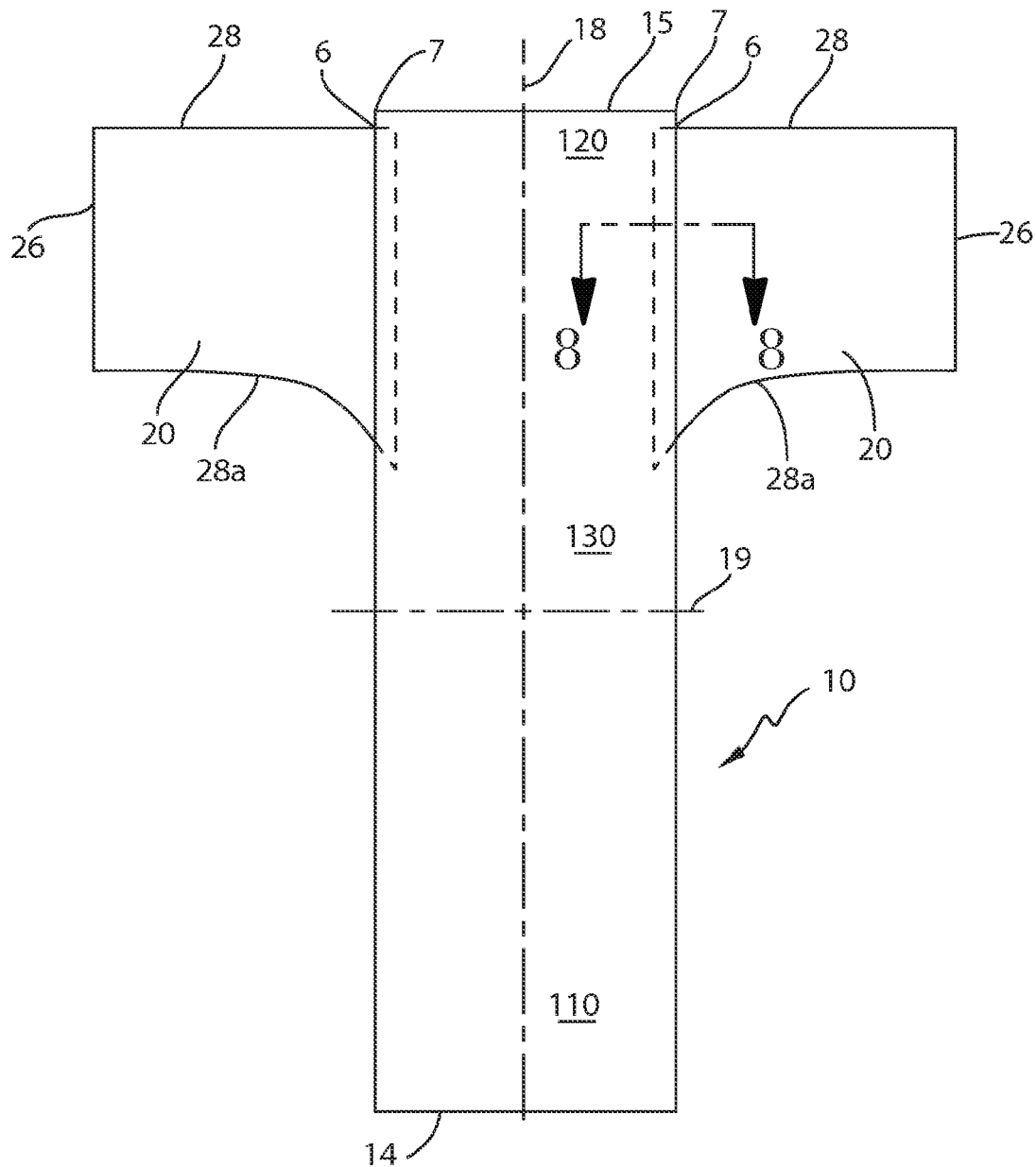
FIG. 1 is a schematic plan view of a precursor structure of a pant including a chassis and side panels, depicted schematically as it would appear with the chassis stretched out to its fullest lateral and longitudinal extents against any contraction caused by elastic members in the chassis, and laid out flat, garment-facing side up.

For purposes of this description, the following terms are given the meanings set forth:

"Elastic", with respect to a member, means the ability of the member, as displayed in a section of material including the member (e.g., a section of side panel laminate), having an initial length prior to loading and a substantially uniform width perpendicular to its initial length, to elongate in length under tensile load applied in the direction of the initial length, without rapture or breakage, by at least 50% of its initial length, as determined by application of the Elongation and Set Test described below. Additionally, following elongation under tensile load by 50% of its initial length, held for a duration of 30 seconds, and subsequent release of the tensile load, an "elastic" member has a set less than or equal to 25% of its initial length, after one loading and unloading cycle and after 1 minute following unloading, performed according to the Elongation and Set Test. For example and by way of illustration, a sample of an "elastic" member that has an initial pre-load length of 50.0 mm can elongate under tensile load at an elongation speed of 250 mm/minute, without rupture or breakage, to at least 75.0 mm (50% elongation). After the sample is held at 50% elongation for 30 seconds and then the tensile load is removed, the sample will contract to a length of 62.5 mm or less within one minute, i.e., have a set of 12.5 mm or less (set of 25% of initial length, or less).

"Film"—means a skin-like or membrane-like layer of material formed of one or more polymers, which does not have a form consisting predominately of a web-like structure of consolidated polymer fibers or other fibers.

"Inner"—with respect to a pant or feature thereof as described herein, generally refers to the inside, or wearer-facing side, of the feature.

"Lateral"—with respect to a pant or feature thereof as described herein, refers to a direction substantially parallel to its waist edges.

"Length"—with respect to a pant or feature thereof as described herein, unless otherwise specified, refers to a dimension measured along a line substantially perpendicular to the waist edges of the pant.

"Liquid impermeable"—means substantially resistive to through-penetration of liquid water and urine at room temperature and ordinary conditions of use.

"Liquid permeable"—means substantially permitting of through-penetration of liquid water and urine at room temperature and ordinary conditions of use.

"Longitudinal"—with respect to a pant or feature thereof as described herein, refers to a direction substantially perpendicular to the waist edges of the pant.

"Mechanical bond site"—means any location at which a bond of and between separate layers of materials is created by (a) compression exerted on and through the layers between bonding rollers or other compressing devices at a compression site ("compression" bond); (b) localized application of heat, ultrasonic or other heating energy exerted on and through the layers ("thermal" or "ultrasonic" bond); or (c) a combination of compression exerted on and through the layers between bonding rollers or other compressing devices at a compression site together with heat, ultrasonic energy or other heating energy directed to the compression site ("combination" bond), to effect localized deformation, physical entanglement and/or fusing, or a combination thereof of the separate layers of materials at or about the bond site. As used herein, "mechanical bond" also means and is limited to a bond that cannot be reestablished merely by urging materials together by hand at room temperature following a forcible separation thereof, in that forcible separation of the bonded layers effects destruction of the physical structure at or about the bond site.

"Nonwoven"—means any cloth-like, web-like and/or sheet-like material formed of consolidated polymer fibers that are neither knitted nor woven.

"Outer"—with respect to a pant or feature thereof as described herein, generally refers to the outside, or garment-facing side, of the feature.

"Proximate to"—when one of two features is described as the one "proximate to" a third feature, "proximate to" identifies which feature of the first two is closest to the third.

"Width"—with respect to a pant or feature thereof as described herein, unless otherwise specified, refers to a dimension measured along a line substantially parallel to the waist edges of the pant.

DESCRIPTION

Referring to FIG. 1, a disposable absorbent pant according the present invention may be formed of a precursor structure having a chassis 10, having a first waist region 110, a second waist region 120, and a crotch region 130 between the first and second waist regions. A longitudinal center line 18 and a lateral center line 19 may be identified, that equally divide the width and length, respectively, of the chassis 10. The crotch region 130 may constitute about 33 percent to about 50 percent of the chassis length, and correspondingly, each waist region may constitute about 25 percent to about 33 percent of the chassis length.

Additional chassis details are schematically represented in exploded cross-section in, e.g., FIGS. 7A-7D; 8A-8G; 9, 10, 14A-14E, and 14A-15B. The chassis 10 may include an inner, body-facing, liquid-permeable topsheet 30, an absorbent core 40, and an outer, garment facing, liquid-impermeable backsheet 49 formed of a liquid-impermeable polymer film layer 50 and an outer backsheet nonwoven layer 52. The liquid-impermeable polymer film layer 50 of backsheet 49 may be included to provide liquid containment capability to the chassis, (Generally, the fine dotted lines in the figures schematically represent deposits of adhesive that may be included to bond layers together, whether specifically identified or not in the following description.) Chassis 10 also may include various other features (not specifically shown) such as additional layers of containment, liquid acquisition and/or distribution material, etc.

Figure 7A:
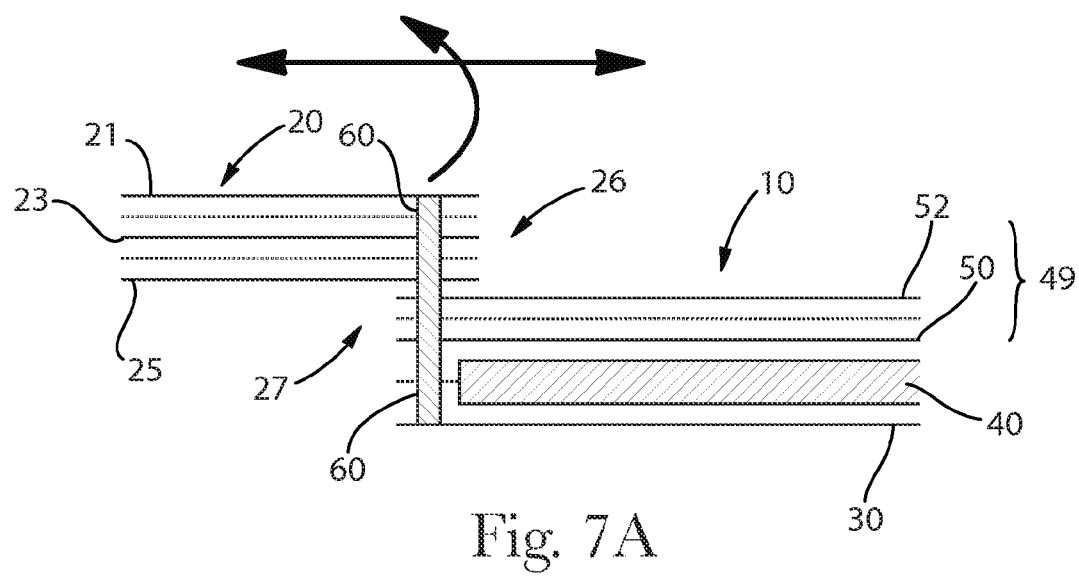
FIG. 7A is a schematic, exploded, lateral cross-sectional view of a seam having an overlapping configuration, and portions of a chassis and side panel at the seam arranged in one configuration.

Referring to FIGS. 1 and 7A, the precursor structure also includes a pair of laterally opposing side panels 20 that extend laterally from the chassis 10. Side panels 20 are laterally elastically extensible and contractible. Each of side panels 20 may be a single, continuous section of material (i.e., having no intermediate seams joining separate sections) cut from a web of stretch laminate material, the stretch laminate material formed of outer and inner layers of side panel nonwoven 21, 25, with an elastic member 23 sandwiched therebetween. The stretch laminate may be formed of materials and activated to enable lateral stretch by incremental stretching, by materials and methods, to produce laminate described in, for example, U.S. Pat. Nos. 5,167,897; 5,156,793; and 5,143,679; or U.S. application Ser. Nos. 10/288,095; 10/288,126; 10/429,433; 11/410,170; 11/811,130; 11/899,656; 11/899,810; 11/899/811; 11/899,812; 12/204,844; 12/204,849; 12/204,854; 12/204,858; or 12/204,864, the disclosures of which are incorporated herein by reference. As an alternative to formation by the above-referenced methods, a stretch laminate may be formed laminating an elastic member in a pre-stretched condition to one or more layers of nonwoven in a substantially unstretched condition. When the resulting laminate is allowed to relax, the nonwoven layer(s) form gathers or rugosities of gathered material transverse to the direction of stretch of the elastic member, which are then available to permit and accommodate stretching of the laminate along the direction of pre-stretch of the elastic member. Elastic member 23 may be one or more longitudinally-spaced laterally extending strips of an elastomeric material, or a continuous layer of elastomeric film. Alternatively, elastic member 23 may be one or more laterally extending, longitudinally-spaced strands of elastomeric material, or a scrim material having elastomeric strand components. Materials forming side panels 20 may be joined or integrated with materials of the chassis 10 in various ways as will be hereinafter described.

Figure 2:
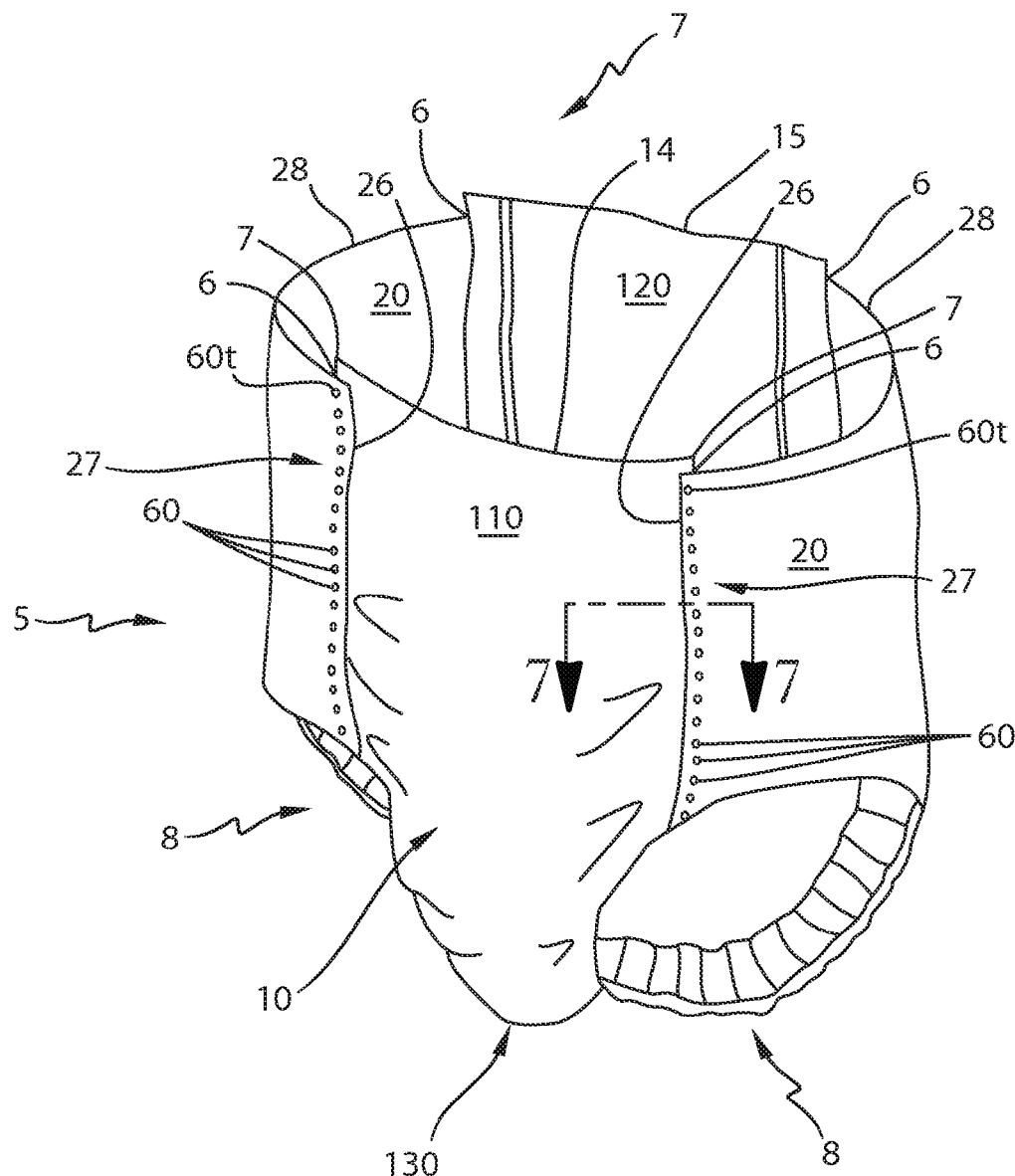
FIG. 2 is a perspective view of an assembled pant.

Referring to FIGS. 1 and 2, a disposable absorbent pant 5 (FIG. 2) may be formed by folding chassis 10 at or about lateral center line 19 to bring waist regions 110, 120 together, topsheet 30 facing inwardly, and then by joining the materials of side panels 20 near seam edges 26 thereof, to materials of chassis 10, in various ways as will be hereinafter described. The resulting absorbent pant 5 is a pant-like structure having leg openings 8 and waist opening 7, with side panels 20 each formed of a single section of material. The pant may be donned by insertion of the wearer's feet into waist opening 7 then back out through leg openings 8, and then by pulling the pant by one or more of waist/top edges 14, 15, 28 up and over the wearer's legs and buttocks and into place about the lower torso, like a pair of underpants or briefs. The lateral stretch capability of the side panels 20 allows the pant to elastically expand laterally or hoop-wise to ease its passage over body contours while being donned, and then elastically contract to provide a secure fit while in wearing position on the wearer's body.

Seam Location Indicia

Side panels 20 may be formed of a stretch laminate material that is manufactured of one or more layers of material that are distinct from materials forming chassis 10. As such, these materials may be tinted or printed to impart color that provides a visual contrast with materials forming chassis 10. Referring to FIG. 2, side panels 20 may be formed of materials having, or printed to have, one or more colors that contrast with, e.g., color(s) of materials forming waist regions 110, 120 of chassis 10, and particularly backsheet 49 (see, e.g., FIG. 7A). Alternatively, the materials forming side panels 20 may be untinted, while materials forming backsheet 49, such as polymer film layer 50 and/or outer backsheet nonwoven layer 52, may be tinted or printed in colors that contrast with side panels 20. Alternatively, materials forming both side panels 20 and backsheet 49 may be tinted and/or printed, but in contrasting colors.

The resulting visual contrast between chassis 10 and/or backsheet 49, and side panel 20, can be exploited to provide a visible indicium of the locations of seams 27 joining side panels 20 to waist regions 110, 120. This visible indicium may be useful, to a wearer or caregiver, for identifying location(s) at which the seam(s) may be separated by tearing, made more convenient by the overlapping configuration described below.

For purposes herein, a "visual contrast" between a side panel and a chassis is created when a clearly and readily apparent contrast exists, or at a minimum, where the calculated value ΔE* (a value calculated based on the measured values in the CIE L*a*b* color scale for respective specimens of the backsheet and side panel, according to the color measurement method set forth below) is 3.0 or greater.

Strong but Conveniently Tearable Side Panel Seams

Referring to FIG. 7A, side panels 20 may be joined to chassis 10 by seam 27 having an overlapping configuration as schematically depicted. In this overlapping configuration, all components of side panel 20, including outer side panel nonwoven layer 21, elastic member 23, and inner side panel nonwoven layer 25, overlie all components of chassis 10, to the outside thereof. Where the above-described visible indicium of a tearing location is desired, and contrasting colors for chassis materials and side panel materials are selected, this configuration provides such visible indicium readily identifying a seam location.

The overlapping configuration illustrated, however, has some disadvantages unless mitigating features are included. The illustrated overlapping configuration provides a relatively small, singularized surface area of respective chassis materials and side panel materials available to be bonded and joined. As may be appreciated from FIG. 7A, only a relatively small strip of contact area between inner side panel nonwoven layer 25 and outer backsheet nonwoven layer 52 is provided at seam 27. Additionally, lateral tension across seam 27 in the direction of the double-headed arrow as illustrated in FIG. 7A will create a moment tending to cause the seam to rotate slightly in the direction indicated by the curved arrow, which results in a combination of both shear stress and normal stress in the seam, increasing the likelihood of a failure of the seam.

Thus, for purposes of providing suitable lateral hoop tensile strength of the pant, and reducing the chances of a loss of elastic contraction or even failure resulting from delamination and/or decoupling of elastic member 23 from other layers 21, 25 of side panel 20 resulting from stretching, it may be desirable in many circumstances that a bond securely bonding and unitizing elastic member 23 with materials forming, at least, backsheet 49, if not the entire chassis envelope structure formed by backsheet 49 and topsheet 30. Accordingly, it may be desirable that with an overlapping construction as illustrated, a plurality of mechanical bond sites 60 are provided, which penetrate through, and bond, all layers of stretch panel 20 to each other, and also with at least all layers of backsheet 49, and, even more desirable in some circumstances, all layers of the chassis 10 underlying the overlapping stretch panel 20, including topsheet 30, liquid-impermeable polymer film layer 50, and outer backsheet nonwoven layer 52. This type of bonding marries the strengths of all of the layers at the seam 27 to provide a relatively strong seam 27 for the overlapping configuration illustrated.

Referring to FIGS. 2 and 7A, a plurality of mechanical bond sites 60 at seams 27 may be discrete, spaced apart from each other, and lie along a single line or path defined by a bonded area (bond site) followed by an unbonded area followed by a bonded area . . . and so on. Such a line or path of intermittent mechanical bonding may be created by suitably configured mechanical bonding equipment and provides several advantages.

Referring to FIG. 7A, it can be seen that mechanical bonds 60 penetrating and bonding together outer side panel nonwoven layer 21, elastic member 23, inner side panel nonwoven layer 25, outer backsheet nonwoven layer 52, liquid-impermeable polymer film layer, and, optionally, topsheet 30, serve to anchor elastic member 23 to chassis 10. This enables the manufacturer to minimize the amount of material forming elastic member 23 that extends past bonds 60, overhanging the seam (with respect to FIG. 7A, to the right)—i.e., minimize elastomeric material that is wasted at the seam because its stretch functionality is not utilized to provide stretch capability to the pant.

Figure 3:
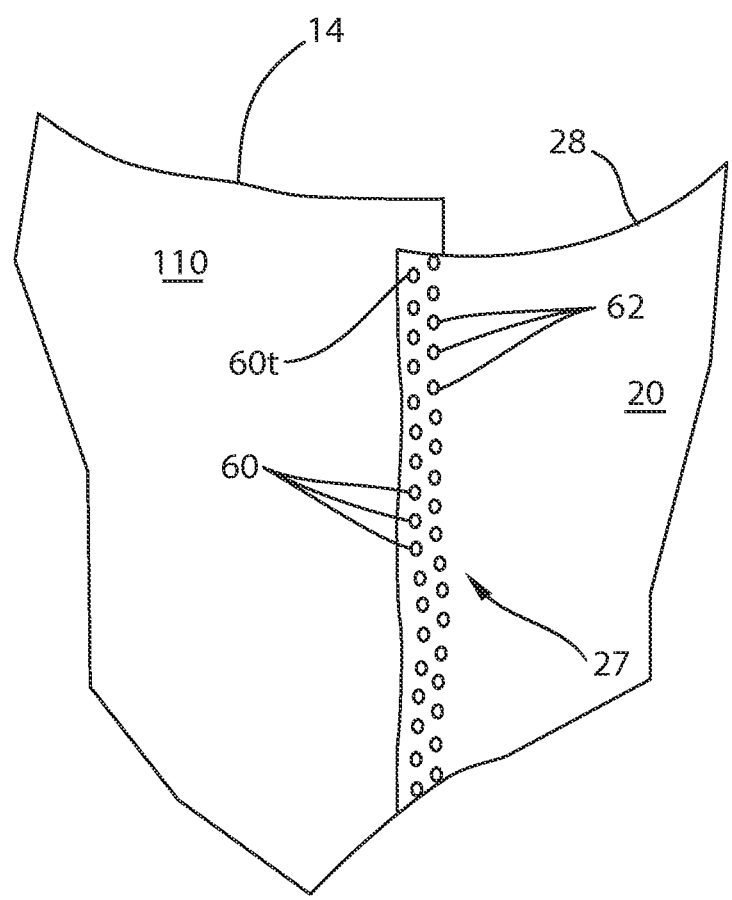
FIG. 3 is a perspective outside view of an overlapping seam on an assembled pant.
Figure 4:
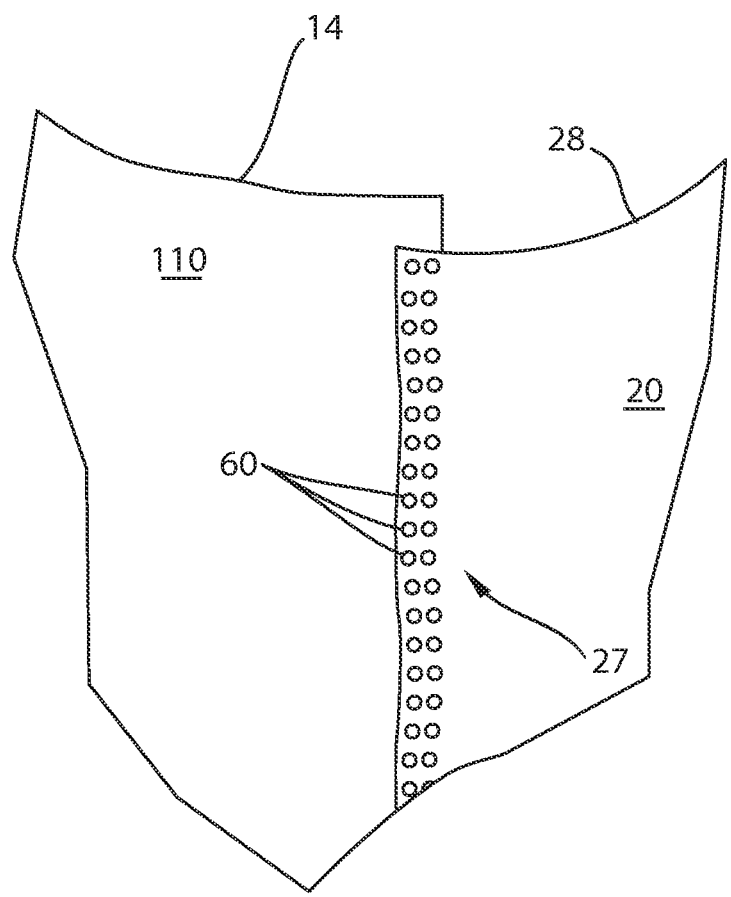
FIG. 4 is a perspective outside view of an overlapping seam on an assembled pant.

As noted previously, it may be desirable that seam 27 be conveniently tearable to enable quick and neat removal of the pant when, e.g., it is soiled. If seam 27 were bonded by a continuous, elongated bond site along the length thereof, a neat tear propagating along the seam may be difficult or unlikely. With the plurality of discrete, spaced apart bond sites 60 lying along a single line or path as suggested in FIG. 2, however, lateral, longitudinal and/or normal forces manually exerted by the wearer or caregiver gripping the pant at the top (waist edge) and pulling across a seam 27 (i.e., when the wearer or caregiver pulls the top corner and front edge of side panel 20 downwardly relative waist region 110), initially concentrates such forces to a significant extent about the top-most discrete bond site 60t, making breaking the bond or the materials about the bond at that single site relatively easy. When the bond at, or materials about, the top-most bond site 60t break, sudden acceleration of the wearer/caregiver's gripping hands pulling away from each other, resulting from the materials "letting go," at the bond site 60t, together with continued pulling forces exerted, can cause the next bond site down the path to be attacked with equal or greater concentrated separating force, resulting in a quick material break, and so on, each subsequent bond along the path being attacked by concentrated separating forces individually, in a sequential, zipper-like fashion. This mode of tearing of the seam is enabled by the unbonded areas between the sequential bond sites 60, which allow for the acceleration following each discrete bond break, as described above. It will be appreciated that, to achieve the zipper-tear effect described above, it may be desirable that the seam 27 have no parallel second line or path defined by bond sites 62 (such as illustrated in FIG. 3) that are longitudinally offset from bond sites 60 in such a manner as to substantially reduce or eliminate the advantage provided by the unbonded areas along the first path. In other words, it may be desirable that the above-described acceleration between bond breaks be enabled, not substantially interrupted by bonds along or adjacent the tear path. Accordingly, a single line, path or row of bond sites 60 along a seam 27 (as illustrated in FIG. 2) may be desired in some circumstances. Alternatively, a plurality of paths or rows of bond sites may be employed, as not to be longitudinally offset, as suggested by FIG. 4), or otherwise arranged to provide a tear propagation path lying along a path of discrete, spaced apart bonds separated by unbonded areas. This will preserve the zipper-tear effect described above.

The size, shape and spacing of the mechanical bond sites 60 may be adjusted (via corresponding configuration of the mechanical bonding equipment) to strike a desired balance between seam strength and convenient tearability. Without intending to be bound by theory, it is believed that the strength, or ability of a mechanical bond to hold respective lapped, bonded web materials together against applied shearing forces, resides in a perimeter "grommet" of deformed, entangled and/or fused materials that have been expressed from the interior of the bond site out toward the perimeter, under pressure exerted by the bonding equipment. It is believed preferable that bond sites be circular or rounded, having no sharp angles about their perimeters, to avoid concentrations of stresses that such features would promote, and conversely, to promote the smooth distribution of stresses about the perimeter "grommet". It is believed, further, that a greater number of relatively smaller bond sites can have comparatively greater holding strength than a smaller number of relatively larger, similarly-shaped bond sites occupying the same total bond site area, because the greater number of smaller sites will have total combined perimeters, having surrounding "grommet"formations, exceeding that of the fewer number of larger sites. At the same time, however, bond sites cannot be too small, because, as bond site size/area is decreased, a point is reached where there will be insufficient material available within the bond site area to be expressed out to the perimeter, to form a substantial "gromrnet" of deformed, entangled and/or fused materials.

Figure 5:
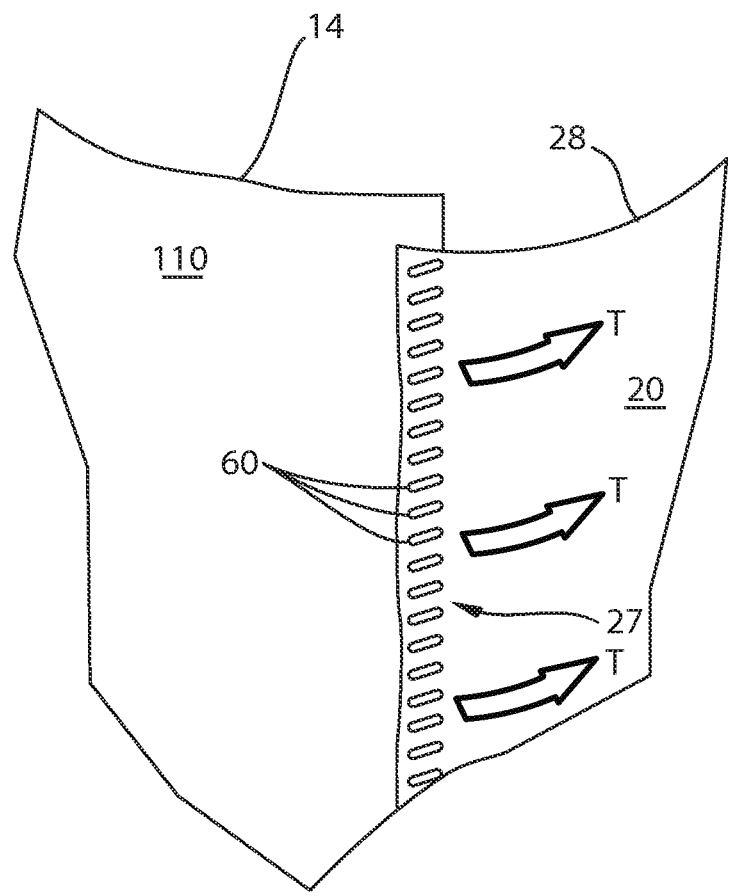
FIG. 5 is a perspective outside view of an overlapping seam on an assembled pant.
Figure 6:
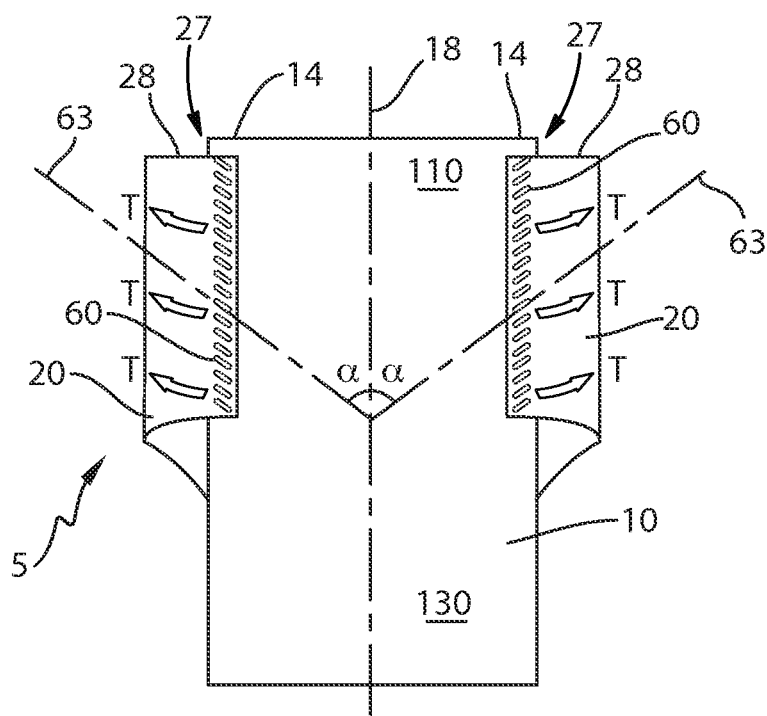
FIG. 6 is a schematic outside front view of an assembled pant in an upright position.

Without intending to be bound by theory, it is believed that lateral lines of tension T in the pant during wear often tend to be inclined front-to-rear as suggested in FIGS. 5 and 6 (where the pant is configured such that waist region 110 is the front region) as a result of wearer body contours and force distribution when the article is loaded with exudates, as explained in, e.g., PCT App. No. WO 2007/141749 by Lodge. In one alternative mechanical bond pattern, a plurality of individual, spaced-apart mechanical bond sites 60 may be disposed in a path and configured in a manner having characteristics such as suggested in FIGS. 5 and 6, to provide both convenient tearability and satisfactory lateral seam strength. Referring to these figures, it can be seen that individual mechanical bond sites 60 may be of rounded elongate, oblong, oval, ovaloid, elliptical or other rounded elongate shapes that have their longest dimensions measurable along directions that are inclined as they move laterally away from longitudinal center line 18 of chassis 10, as viewed with pant 5 in an upright orientation as suggested in FIG. 6—a direction illustrated by inclined lines 63. Without intending to be bound by theory, it is believed that a mechanical bond configuration having characteristics suggested in FIGS. 5 and 6 may provide satisfactory lateral seam strength because, when the bond sites are appropriately configured, generally, shearing stresses resulting from most or all lateral lines of tension T in the side panel 20 may be distributed along the greater lengths of the mechanical bonds at the seam. Thus, the depicted mechanical bond site arrangement may be quite resistant to unintentional tearing resulting only from lateral forces in the pant occurring during normal wear, as compared with other possible bond patterns. Without intending to be bound by theory, it is believed further, however, that upon a combination of the differing lateral, longitudinal and normal separating forces exerted across a seam 27 by a wearer or caregiver gripping chassis 10 along waist edge 15 and side panel 20 along top edge 28 with either hand, respectively (i.e., when the wearer or caregiver pulls the top corner and front edge of side panel 20 downwardly relative waist region 110), the depicted incline of the elongate mechanical bond sites 60 promotes tear propagation in the side panel 20 along the outlines of the elongate shapes, directed downward and toward longitudinal center line 18 (i.e., approximately along the direction of inclined lines 63), providing for relatively easy tearing propagating downward along seam 27 with minimized likelihood of tear propagation away from seam 27 into the remainder of side panel 20. The angle $\alpha$ formed by either of inclined lines 63 with respect to longitudinal center line 18 may be in range of about 15 degrees to about 75 degrees, more preferably about 25 degrees to about 60 degrees, and even more preferably about 30 degrees to about 50 degrees.

In a variation of the seam configuration depicted in FIG. 7A, rather than side panel 20 being disposed such that it overlaps chassis 10 over outer backsheet nonwoven layer 52, i.e., rather than it being disposed such that it overlaps chassis 10 on the outside (garment-facing side) thereof, and overlies layer 52, side panel 20 may be disposed such that backsheet 49 and/or entire chassis 10 overlap/overlie side panel 20 on the outside (garment-facing side) thereof. See FIG. 7D. Thus, each of side panel layers 21 and 25, and optionally, layer 23, may be disposed to the inside of backsheet 49 and even chassis 10, including topsheet 30. Layers 21 and 25, and optionally, layer 23, may also be bonded to the chassis at mechanical bond sites 60, as described above.

Figure 7B:
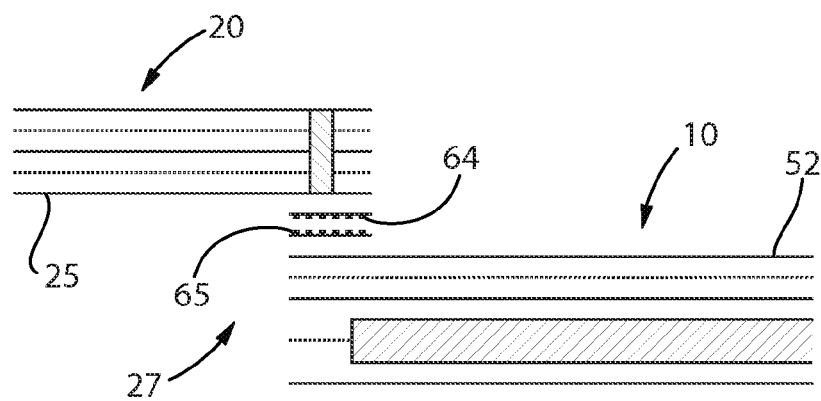
FIG. 7B is a schematic, exploded, lateral cross-sectional view of a seam having an overlapping configuration, and portions of a chassis and side panel at the seam arranged in an alternative configuration.
Figure 7C:
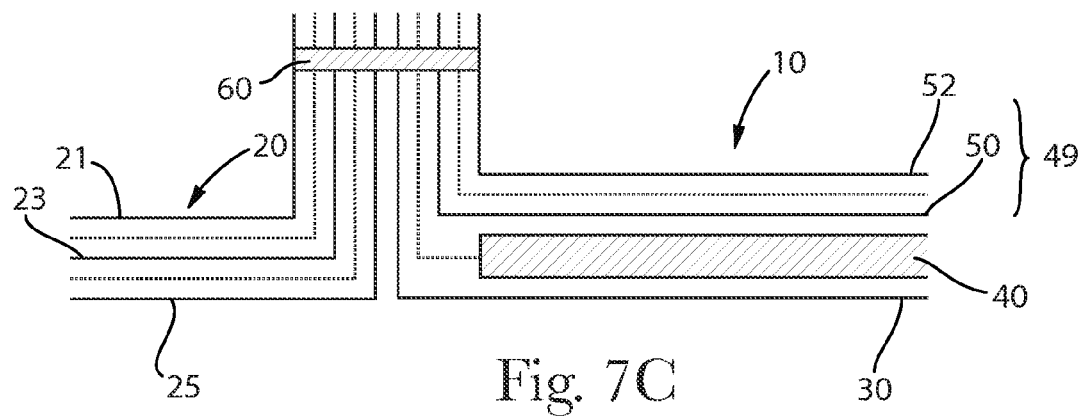
FIG. 7C is a schematic, exploded, lateral cross-sectional view of a seam having an abutting configuration, and portions of a chassis and side panel at the seam arranged in an alternative configuration.
Figure 7D:
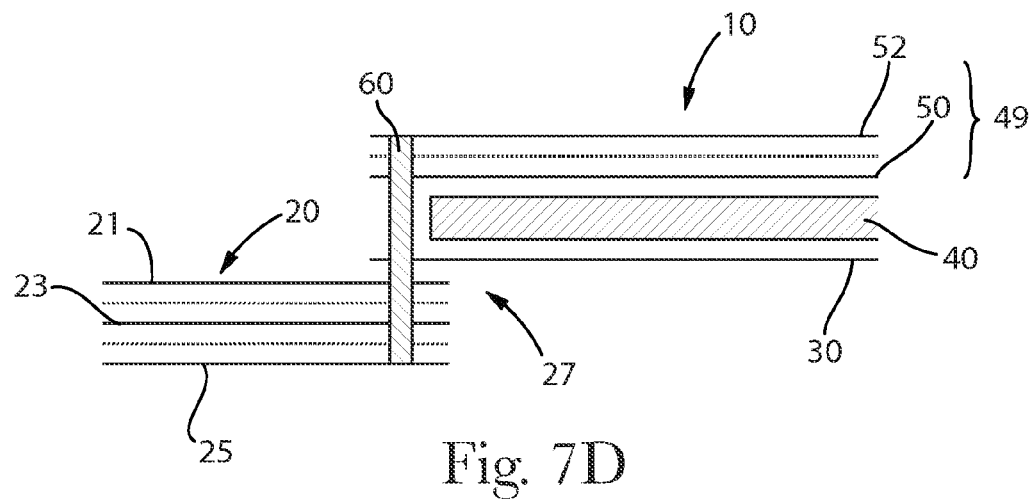
FIG. 7D is a schematic, exploded, lateral cross-sectional view of a seam having an overlapping configuration, and portions of a chassis and side panel at the seam arranged in an alternative configuration.

In another alternative, it may be desired to form a seam in an abutting configuration as depicted in FIG. 7C. It can be seen that, in this configuration, all layers of side panel 20 still overlap all layers of backsheet 49 and topsheet 30, but with edges turned outward (away from wearer), inside-to-inside (i.e., topsheet 30 facing inner side panel nonwoven layer 25)

arrangement. Mechanical bond sites 60 bond the components together. This abutting seam may be desired in some circumstances, such as, for example, for ease or convenience of manufacturing with particular equipment. It also may enhance tearability in that it enables a wearer or caregiver to exert effective separation forces across the seam that are substantially laterally oriented, thus more intuitive for some wearers or caregivers. On the other hand, it may be appreciated that the abutting seam configuration depicted in FIG. 7C may require relatively more material to form the seam than the configuration shown in FIG. 7A, may result in lower in-use seam strength and/or may present a less refined, less finished or less garment-like appearance, and thus, may not be desired in all circumstances.

From the foregoing it can be appreciated that the combination of overlapping seam configuration described, together with bonding at the seam via a plurality of discrete, spaced-apart mechanical bond sites defining a path or line along the seam, can provide a suitably strong yet conveniently visible and tearable seam.

As an alternative to creating a tearable seam formed of mechanical bonds of the side panel 20 to the chassis 10, an overlapping separable and refastenable seam may be created. Referring to FIG. 7B, a seam 27 having an overlapping configuration similar to that suggested in FIG. 7A is suggested. However, rather than having side panel 20 joined to chassis 10 by mechanical bonds 60 as suggested in FIG. 7A, side panel 20 may be joined to chassis 10 by one or more fastener components 64, 65. For example, a first fastener component 64 may be a patch or strip of hook material forming a component of a hook-and-loop fastening system, and a second facing fastener component 65 may be a patch or strip of loop material forming another component of the system. Respective fastener components 64, 65 may be respectively affixed directly to side panel 20 and chassis 10 by mechanical bonds (not shown) and/or adhesive (not shown). Fastener components 64, 65 may be forcibly but substantially non-destructively separated by a wearer or caregiver gripping the side panel 20 and chassis 10 and exerting separation forces across the seam 27. Appropriately selected fastener components 64, 65 may be substantially non-destructively separable, and refastenable following separation, a function provided by a hook-and-loop system, for example. Other types of fastener components which provide for substantially non-destructive separability and refastenability are available, such as snap fastener components, etc. Additionally, where a hook-and-loop fastening system is chosen, it is not always necessary for a distinct loops component to be included. Some types of nonwovens available have sufficient fiber configuration and bonding characteristics as to be suitable for forming an appropriate attachment surface for a hooks component, and may be chosen to form outer backsheet nonwoven layer 52 or inner side panel nonwoven layer 25, wherein only one fastener component 64 or 65 in the form of a patch or strip of hooks is included and will separably and refastenably engage the nonwoven layer.

An overlapping seam as described above may be used to join a side panel to a chassis at either the front or the rear of the pant, or both. It may be desirable in some circumstances, however, to dispose such a seam at, at least, the front of the pant. For example, where the expected consumer of the product is a caregiver who is accustomed to applying widely-marketed "taped" diapers having fastening "ears" extending from a rear waist portion and wrapping forward around a baby's hips, removably fastening at a front waist area or "landing zone," that consumer may be accustomed to removing such a diaper by lifting the fasteners at the baby's front. Accordingly, that consumer may expect to remove a pant of the type described herein by separating it at the front seams, by pulling stretch panel 20 outwardly away from the chassis 10 front waist region.

Another feature which may be included to enhance wearer/caregiver convenience for tearing is a tophat configuration. Referring to FIGS. 1 and 2, a tophat configuration may be formed by joining side panels 20 to chassis 10 with their top edges 28 longitudinally offset (in the example depicted, downwardly relative a wearer) from chassis waist edges 14, 15. This forms notches 6 and tophat corners 7 along the top/waist edge of the pant, at the locations where the side panels join the chassis. When a wearer or caregiver desires to tear the pant at a seam 27, a notch 6, and associated tophat corner 7, provide several advantages. First, notch 6 provides an additional visual indicium of a tearing location. Second, notch 6 can serve to enhance concentration of tearing forces exerted by the wearer or caregiver, and resulting stresses at the topmost bond site 60t, to better aid in initiating tearing. Third, tophat corner 7 constitutes material that the wearer or caregiver may readily identify and grip on one side of the seam, to exert tearing force. To provide the advantages of the tophat configuration, but also reduce chances of consumer perception of poor quality resulting from an excessive offset or step in the waist edges, it may be desirable that the offset, i.e., height of the tophat corner 7 measured from side panel top edge 28, be about 2 mm to about 15 mm, or more preferably about 3 mm to about 12 mm, or still more preferably about 4 mm to about 10 mm.

A tophat configuration may be such that one or both waist edges 14, 15 extend in a longitudinal direction beyond (or, when the pant is upright, are higher than) side panel top edges 28, (a "positive" tophat configuration) as suggested in FIGS. 1 and 2. However, a pant also may be imparted with a "negative" tophat configuration, such that one or both waist edges 14, 15 are shorter in a longitudinal direction (or, when the pant is upright, are lower than) side panel top edges 28. This "negative" tophat configuration may provide some of the advantages described above, however, the former configuration may be more desirable for aesthetic reasons.

It also may be desirable, where a tophat configuration is provided in combination with an overlapping seam, as described above, that the amount of lateral overlap of the side panel over the backsheet to point at which it is bonded at the bond sites, i.e., the lateral inset of the bond sites 60 toward the longitudinal center line 18 from the longitudinal side edge of the backsheet, be at least 15 mm, i.e., the bond sides at the overlap seam lie laterally inward (relative the chassis 10) of the longitudinal edge of the backsheet 49, and particularly outer backsheet nonwoven layer 52, by at least 15 mm. This overlap may further facilitate tearing of the seam, by giving the wearer or caregiver approximately a finger's width portion of backsheet material to grip that lies laterally over and/or laterally outside (relative the chassis 10) the bonds.

Strong, Aesthetically Appealing and Leak-Resistant Side Panel Seams

Another seam configuration and alternative materials configurations are illustrated in FIGS. 8A-8D and 10. In contrast to the overlapping seam configuration described above, FIGS. 8A-8D and illustrate a sandwiched configuration, in which most or all of the layers forming the side panel at its seam edge 26 are sandwiched between two layers forming the backsheet, and the outer and inner layers of side panel nonwoven 21, 25 are each bonded and/or integral with layers of the backsheet. This sandwiched configuration provides its own advantages.

One set of advantages is attributable to increased material contact surface area as compared with an overlapping configuration seam having the same area of superimposition of respective materials of chassis 10 and side panel 20. As may be appreciated from a comparison of FIG. 8A (sandwiched configuration) with FIG. 7A (overlapping configuration), for the same area A of superimposition of the materials of chassis 10 with the materials of side panel 20, a sandwiched configuration may provide twice as much surface contact area between the respective materials (i.e., along edges of both layers 21, 25 (sandwiched) as compared to along edge of layer 25 only (overlapping). Additionally, if the respective materials are bonded at these contact areas, on the inner and outer surfaces of side panel 20, any rotational moment that might be induced by lateral tension across the seam, such as incidental to the overlapping configuration, is either not present or is substantially reduced by the sandwiched configuration. Thus, lateral tension across seam 27 more likely creates only, or mostly, shearing stresses in the seam. An adhesive bond formed of the type of adhesive typically used to assemble articles of this type is more capable of resisting shearing stress than normal stress under ordinary conditions of use. Thus, a sandwiched configuration makes joining of separate elements by only adhesive bonding more capable (as compared with an overlapped configuration) of providing sufficient strength in a seam joining a side panel to a chassis.

Figure 8A:
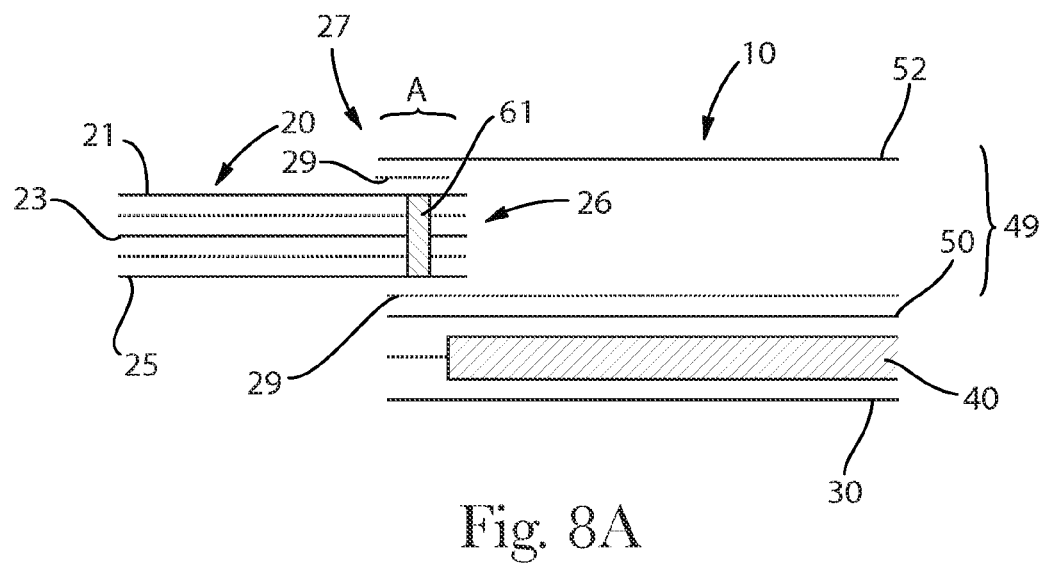
FIG. 8A is a schematic, exploded, lateral cross-sectional view of a seam having a sandwiched configuration, and portions of a chassis and side panel at the seam arranged in one configuration.
Figure 8B:
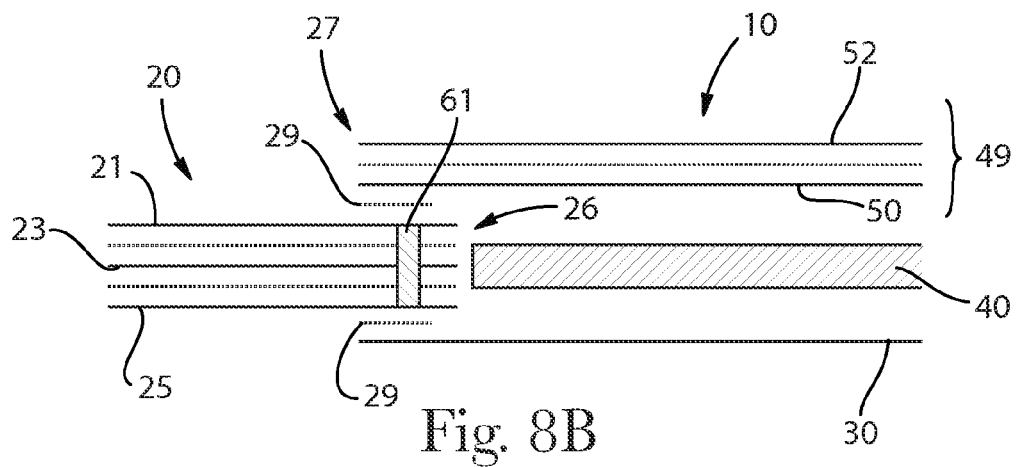
FIG. 8B is a schematic, exploded, lateral cross-sectional view of a seam having a sandwiched configuration, and portions of a chassis and side panel at the seam arranged in an alternative configuration.

In many circumstances it may be preferable to adhesively bond a side panel directly to the polymer film layer 50 of the backsheet 49 as suggested in FIG. 8A, because, in many types of backsheets the polymer film layer is the layer that contributes the greater proportion of overall lateral tensile strength and dimensional stability to the backsheet. Thus, sufficient bond strength in a seam 27 having a sandwiched configuration (e.g., FIG. 8A) may be achieved merely through use of concealed seam adhesive deposits 29 bonding the inner and outer surfaces of side panel 20 within/between layers of backsheet 49, as suggested in FIG. 8A. In another alternative, a sandwiched configuration as depicted in FIG. 8B may be used. It can be seen in FIG. 8B that side panel 20 may be situated between polymer film layer 50 and topsheet 30, and bonded therebetween by deposits of adhesive 29. This configuration may serve to take advantage the greater opacity of the entire backsheet layer 49, providing better outward concealment of the seam 27, while still bonding side panel 20 directly to polymer film layer 50.

Other advantages may be provided by the described sandwiched configuration. Since the seam may be formed with no externally exposed bonds, a clean and neat, finished outward appearance may be provided. Sufficient adhesive bonding strength may be provided such that mechanical bonding is unnecessary. This may be desirable where perforation or damage to the liquid-impermeable polymer film layer 50 forming the backsheet, typically caused by mechanical bonding and possibly compromising its liquid containment capability, is to be avoided. With an absorbent pant of the kind described herein, this may be desirable particularly in the rear region of the chassis, which may be required to contain liquid expressed from the core when it is compressed, e.g., when the wearer sits on a urine-loaded core. For the foregoing reasons it may be desirable that seams 27 joining the side panels 20 to the chassis 10 in the rear region of the pant have a sandwiched configuration.

In some circumstances, it may be desirable to ensure that elastic member 23 is anchored at the seam. This may be deemed desirable in constructions where lateral tension applied to side panel is likely to cause delamination of the stretch laminate forming the side panel, and lateral contraction of elastic member 23 within and relative to nonwoven layers 21, 25 causing loss of the elastic contraction functionality of the side panel. Anchoring elastic member 23 at the seam can serve to avoid such loss. Accordingly, prior to being joined to chassis 10, the material forming side panel 20 may have one or more mechanical bonds 61 formed along edge 26, anchoring elastic member 23 to layers 21 and 25.

Figure 8C:
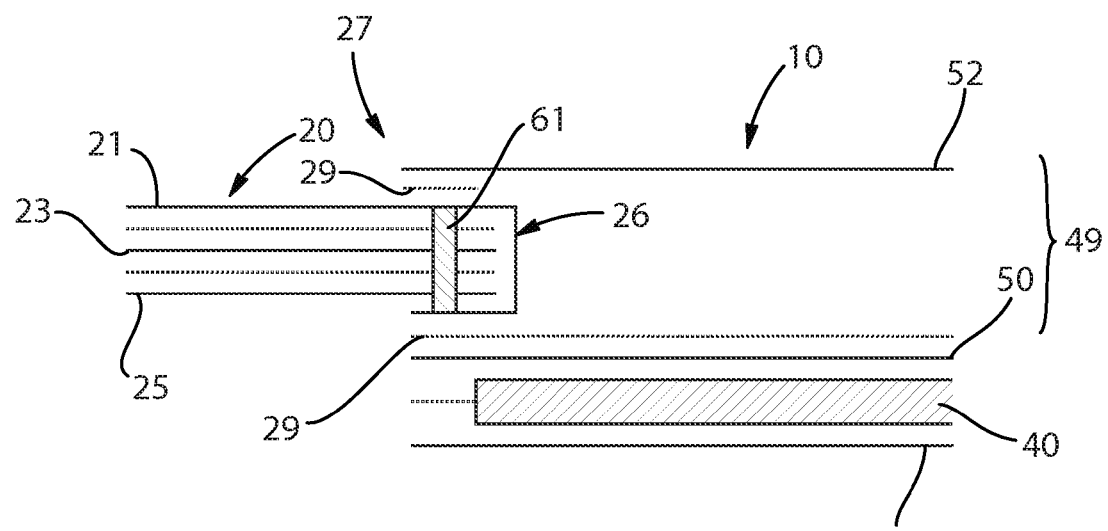
FIG. 8C is a schematic, exploded, lateral cross-sectional view of a seam having a sandwiched configuration, and portions of a chassis and side panel at the seam arranged in an alternative configuration.
Figure 8D:
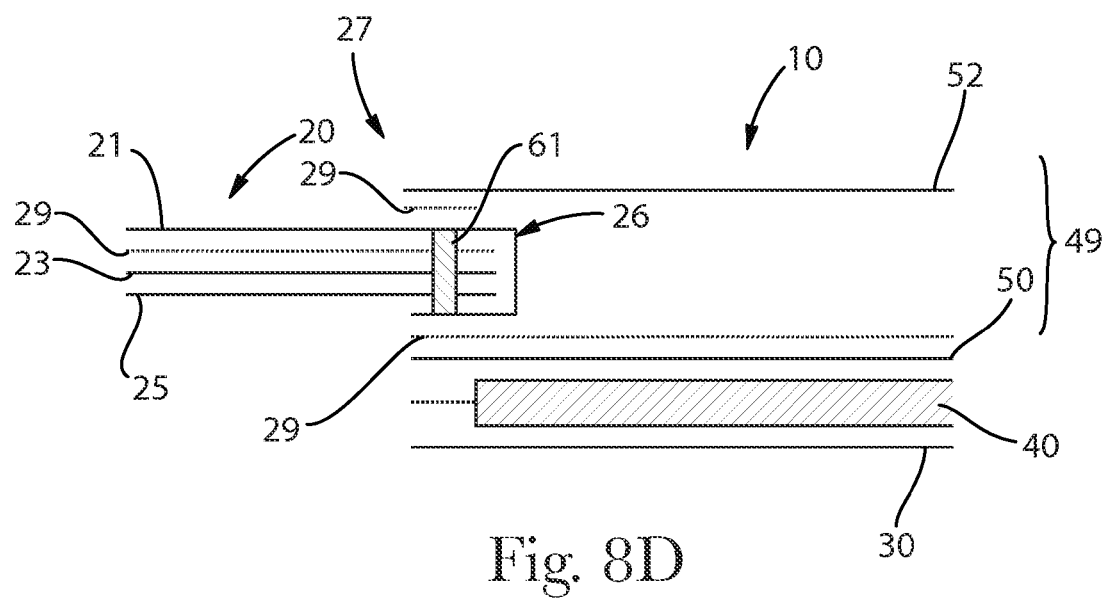
FIG. 8D is a schematic, exploded, lateral cross-sectional view of a seam having a sandwiched configuration, and portions of a chassis and side panel at the seam arranged in another alternative configuration.
Figure 10:
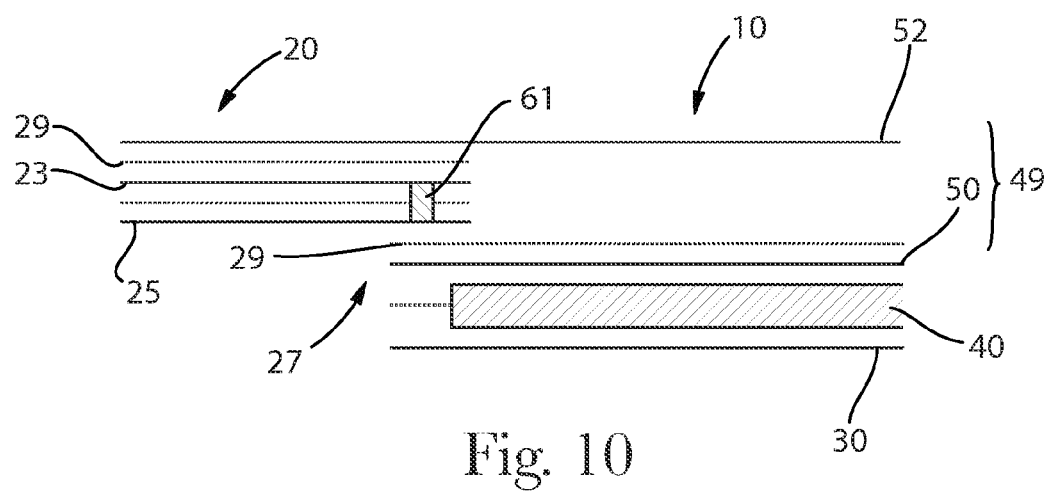
FIG. 10 is a schematic, exploded, lateral cross-sectional view of a seam having a sandwiched configuration, and portions of a chassis and side panel at the seam arranged in another alternative configuration.

Alternative configurations of materials and seams in a sandwiched configuration are depicted in FIGS. 8C, 8D and 10.

Referring to FIGS. 8C and 8D, it can be seen that outer side panel nonwoven layer 21 may wrap over and around inner side panel nonwoven layer 25, along edge 26. Layer 21, elastic member 23 and layer 25, together with the wraparound portion of layer 21, may be bonded by one or more mechanical bonds 61 as suggested in FIG. 8C, thereby providing anchoring of elastic member 23 at the seam. In some circumstances one of inner or outer side panel nonwoven layer 21 or 25 and elastic member 23 may be joined in a process by which melted or softened elastomeric material is extruded or otherwise applied onto the nonwoven layer and adheres thereto without the need for adhesive, to form a precursor laminate including an elastomeric film laminated with a layer of nonwoven. Such a precursor laminate may be produced in a process prior to and separate from the pant manufacturing process, and procured as such for use in the pant manufacturing process. During the pant manufacturing process, the other of inner or outer side panel nonwoven layer 21 or 25 may be joined/laminated with elastic member 23 using a deposit of adhesive therebetween to adhere them together. This procurement and manufacturing procedure may reduce the need for adhesive and may be economically efficient in some circumstances. In the resulting laminate there will be an area thereof comprising a substantial portion or all of the laminate in which a separate deposit of adhesive between one of nonwoven layers 21 or 25 and an elastomeric film forming elastic member 23 is not present, while a deposit of adhesive 29 added during the manufacturing process to laminate the other of nonwoven layers 21 or 25 to the elastomeric film is present. When the resulting side panel 20 is cut from the laminate, a substantial portion or all of the side panel may have no substantial deposit of adhesive between one side of the elastic member 23 and one side panel nonwoven layer 25 laminated thereover, as suggested in FIG. 8D, while having a deposit of adhesive 29 on the other side of elastic member 23 to adhere elastic member 23 to the other side panel nonwoven layer 21. In such circumstances using the wrap-around configuration of layer 21 as suggested in FIG. 8D may be desirable to enhance anchoring of the film along edge 26.

Referring to FIG. 10, it can be seen that side panel 20 may be partially integral with backsheet 49, by sharing a common outer backsheet/side panel nonwoven layer 52. Elastic member 23 may be anchored at the seam by one or more mechanical bonds 61. Elastic member 23 and inner side panel nonwoven layer 25 as discrete components may be bonded to chassis 10 by adhesive deposits 29. This arrangement provides a strong, partially integral junction between side panel 20 and chassis 10, secure anchoring of elastic member 23 at the seam, and a clean, neat, smooth outward appearance along seam 27, because the seam may be partially or substantially concealed by the common outer backsheet/side panel nonwoven layer 52.

Extended Stretch Capability with Maintenance of Snug Fit

Another advantage afforded by the sandwiched configuration described herein is that, with a variation thereof to be described, the lateral, hoop-wise stretch capacity of the pant can be increased by increasing the lateral width of the side panels, without compromising the neat outward appearance of the sandwiched configuration and without decreasing the lateral width of the chassis at the waist region, which could detrimentally compromise the lateral width of the chassis envelope available to accommodate the absorbent core; and detrimentally compromise the lateral width of liquid-impermeable backsheet available to contain liquids within the pant. Also, the lateral, hoop-wise stretch capacity of the pant can be increased without increasing the relaxed hoop-wise circumference of the pant, a potentially undesirable adjustment that could result in an undesirably loose and/or insecure fit.

Figure 8E:
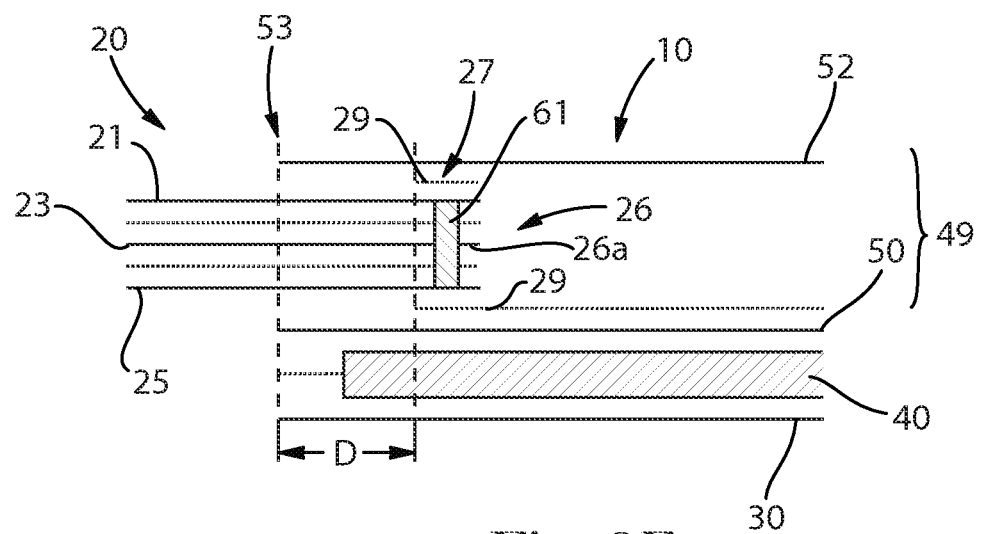
FIG. 8E is a schematic, exploded, lateral cross-sectional view of a seam having a sandwiched configuration, and portions of a chassis and side panel at the seam arranged in another alternative configuration.

Referring to FIG. 8E, it can be seen that seam 27 may be located such that seam 27 affixing side panel 20 to chassis 10 is laterally inset (with respect to FIG. 8E, to the right) a distance D from the longitudinal edge 53 of backsheet 49 and/or backsheet nonwoven layer 52. Seam 27 may be formed by bonds of adhesive deposits 29 near side panel edge 26 as suggested. Portions of side panel 20 lying laterally outward (with respect to FIG. 8E, to the left of) seam 27 may be unbonded to any components of chassis 10, leaving such portions free to laterally stretch independently of components of chassis 10. This configuration provides a way to extend lateral width of the side panel 20, thereby providing additional lateral stretch capacity to the pant, commensurate with the lateral stretch capacity per unit width of the stretch laminate forming side panel 20. This has the advantage of adding stretch capacity to the pant without (a) adding relaxed-state waistband circumference at the risk of creating an undesirably loose- and/or insecurely-fitting pant; or (b) removing chassis or backsheet material at the lateral edges to provide additional lateral room for the added side panel material, i.e., without compromising the lateral width of the chassis envelope that contains the absorbent core, or compromising the lateral width of the liquid-impermeable backsheet material. Additionally, it can be appreciated that the adhesive bonding (adhesive deposits 29, FIG. 8E) made more feasible by the sandwiched configuration does not penetrate or perforate the liquid-impermeable backsheet 49 and particularly the film layer 50, thereby preserving its liquid containment functionality.

Figure 8F:
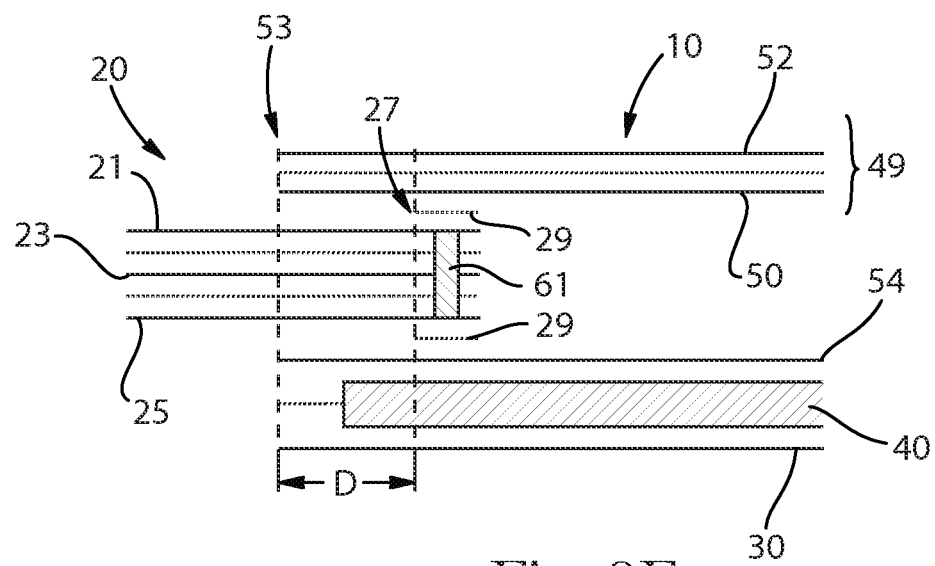
FIG. 8F is a schematic, exploded, lateral cross-sectional view of a seam having a sandwiched configuration, and portions of a chassis and side panel at the seam arranged in another alternative configuration.

In another alternative, the sandwiched configuration depicted in FIG. 8F may be employed. In FIG. 8F it can be seen that, rather than being bonded between polymer film layer 50 and outer backsheet nonwoven layer 52 forming backsheet 49, side panel 20 may be bonded by adhesive deposits 29 between an intermediate layer 54 and polymer film layer 50. This configuration may serve to take advantage the greater opacity of the entire backsheet layer 49, providing better outward concealment of the seam 27, while still bonding side panel 20 directly to polymer film layer 50.

Such extended stretch capability may be provided by disposing seam 27 and the adhesive bonds formed by adhesive deposits 29 at seam 27, at a laterally inset distance D from the laterally outermost longitudinal edge of backsheet nonwoven layer 52 such that, when the materials are in the relaxed state, inset distance D is at least 10% to 50% of the Active Width of the side panel, more preferably, at least 15% to 50% of the Active Width of the side panel, and even more preferably, at least 20% to 50% of the Active Width of the side panel.

Alternatively, sandwiched configuration seams in which seams are laterally inset as described above may be disposed at not just one, but both the first and second chassis waist regions, thereby disposing such extensions of the side panel at both the first and second waist regions. In such a configuration, the total lateral inset distance D of both first and second seams joining a side panel to a chassis (i.e., front and rear seams) may be at least 10% to 50% of the Active Width of the side panel, more preferably, at least 15% to 50% of the Active Width of the side panel, and even more preferably, at least 20% to 50% of the Active Width of the side panel.

For purposes of this description, the "Active Width" of a single-section side panel formed of a stretch laminate is that portion of its width that is not restricted from laterally stretching by bonds at seams, or other structures, and is ordinarily available to provide lateral stretch to the pant structure. Among other methods for causing a side panel of interest to lay flat in a relaxed condition such that its relaxed width can be measured, which will be apparent to those of ordinary skill in the art, the Active Width of a side panel of a particular pant specimen may be determined by using a scissors to cut the chassis laterally across the approximate longitudinal middle of the crotch region of the specimen to separate the first waist region from the second waist region, and cut one side panel longitudinally to separate the first and second waist regions at one side. The resulting dissected pant will consist of the chassis first waist region and the chassis second waist region joined only by the remaining uncut side panel. This structure may be laid relatively flat on a horizontal surface in a relaxed condition to make a width measurement of the side panel. The Active Width of the uncut side panel at any longitudinal location is the width of the side panel, to fullest extent of its relaxed condition, between locations at which the side panel stretch laminate material is bonded to chassis components at seams in the front and rear waist regions. If the side panel is formed of a zero-strain stretch laminate and has an activated (incrementally stretched) zone of a lateral width less than the width of the side panel between bonded locations, and one or more unactivated zones near the seams, the "Active Width" is the width of the activated zone.

From the foregoing description, it can be appreciated that if a side panel is formed of a stretch laminate material that has available lateral stretch before failure of 250% (meaning it will stretch to 2.5 times its relaxed dimension before failure), adding 10% to its Active Width in the manner described adds 25% to its available laterally stretched width; adding 20% to its Active Width adds 50% to its available laterally stretched width, and so on. This gain in available lateral stretch is per side, such that adding side panel width as described at both sides (i.e., both hip areas) of the pant provides double the gain in lateral stretched width per side (thus, in the examples above, 50%, 100%, etc.). At the same time, however, with the construction described, relaxed lateral circumference of the pant is not increased. Thus, a way is provided to both increase lateral stretch available for comfortable and easy donning of the pant, while substantially reducing the risk of creating a pant that is undesirably loose- or insecurely-fitting when in wearing position on a wearer.

The manner of providing extended stretch capability via extension of the side panels as described above may also reduce or eliminate the need for supplementary lateral elastic stretch and contractibility features to be built into the waist regions of the chassis 10 along or proximate the edges 14, 15 thereof (as are included in some currently marketed designs), thereby potentially reducing complexity and cost. Thus, a pant may have the extended side panel construction described above, such that substantial lateral elastic stretch and contraction features and capabilities (e.g., lateral elastic members disposed across one or both of the waist regions along or proximate the end edges 14, 15) are not deemed necessary and are not included, in the front and/or rear waist regions, providing for cost savings.

Additional Material Saving Options
Laterally Shortened Elastic Member

The side panel configuration and seam and bonding configurations described herein also make savings of elastomeric material possible in certain ways.

Figure 9:
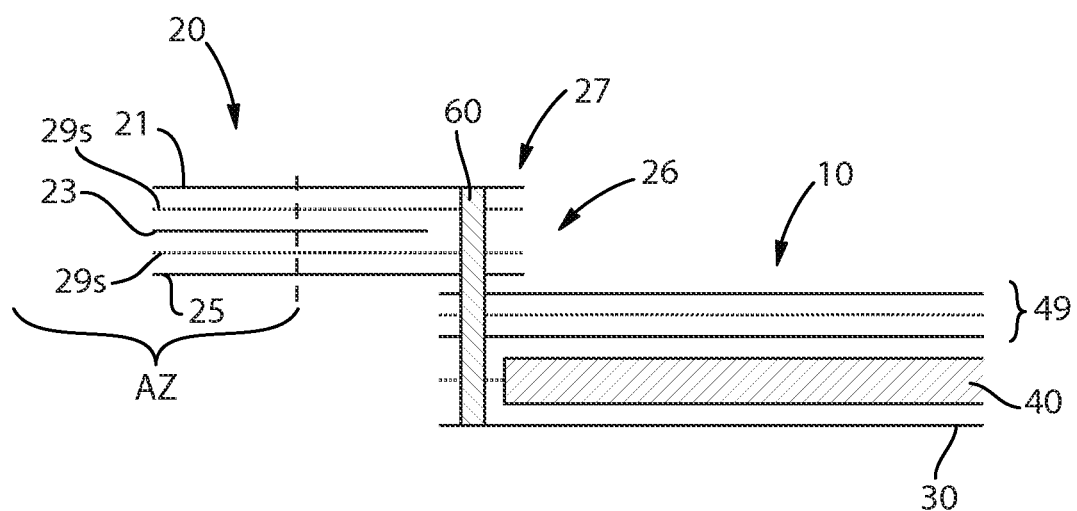
FIG. 9 is a schematic, exploded, lateral cross-sectional view of a seam having an overlapping configuration, and portions of a chassis and side panel at the seam arranged in an alternative configuration.

FIG. 9 depicts a seam 27 having an overlapping configuration and joining side panel 20 with chassis 10. Side panel 20 may be formed of a stretch laminate having outer side panel nonwoven layer 21, elastic member 23, inner side panel nonwoven layer 25, with the layers bonded together by respective adhesive deposits 29s to hold the laminate together. If the design requirements of the particular pant do not require stretchability of the entire lateral width of the stretch panel 20 but only a portion thereof, only activated zone AZ might be incrementally stretched or otherwise activated to render the laminate laterally elastically stretchable, while the portion of stretch panel 20 beyond activated zone AZ (with respect to FIG. 9, to the right of zone AZ) may remain unactivated. This will help reduce the likelihood that elastic member 23 will delaminate from layers 21, 25 under lateral strain, and remain securely bonded therebetween. Thus, the manufacturer may reduce the lateral width of elastic member 23 such that it is not as great as that of layers 21, 25, as suggested in FIG. 9. This provides savings in the elastomeric material required to form elastic member 23. In another alternative (not depicted), layers 21, 23 and 25 may be bonded together along the edge of elastic member 23 by one or more mechanical bonds to anchor elastic member 23 to layers 21 and 25.

Figure 8G:
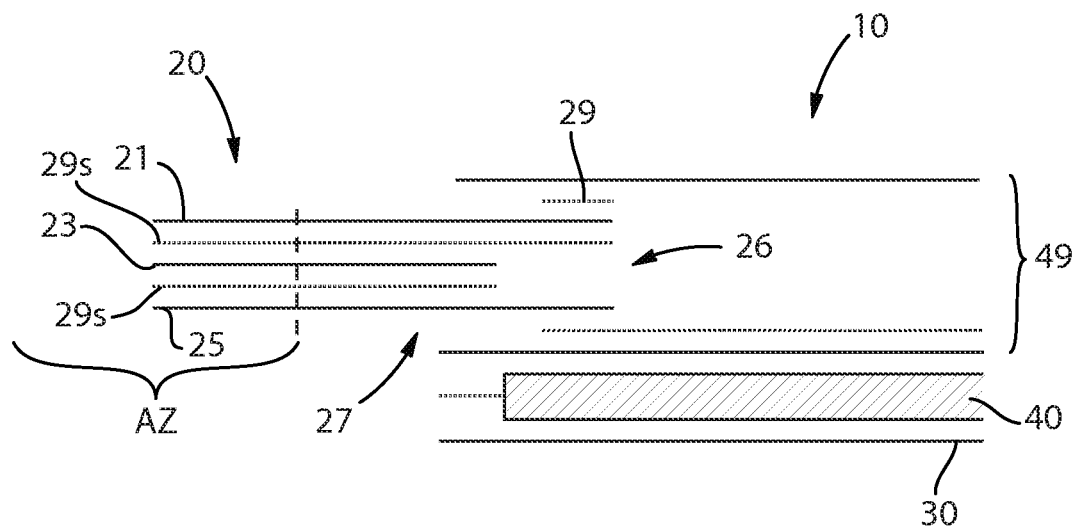
FIG. 8G is a schematic, exploded, lateral cross-sectional view of a seam having a sandwiched configuration, and portions of a chassis and side panel at the seam arranged in another alternative configuration.

FIG. 8G depicts a seam 27 having a sandwiched configuration and joining side panel 20 with chassis 10. From the description in the preceding paragraph applied in the context of FIG. 8G, a similar way of savings of elastomeric material can be appreciated in the context of a seam having a sandwiched configuration.

Cuff Design and Combination Seam

As may be appreciated from the figures, the lateral waist circumference or hoop length of the pant is taken up by the chassis materials forming the envelope containing the absorbent core 40, the side panels 20, and any longitudinal seams joining the side panels 20 to the chassis. Seams (and the portions of materials necessary to form them) are necessary to join dissimilar materials and/or separate components. However, seams usually provide neither stretch capability (as do the side panels 20), nor envelope space for the absorbent core 40. Thus, it may be desirable to minimize the lateral width of seams and/or to structure seams so as to maximize those portions of the lateral waist circumference of the pant available to be taken up by either side panels 20 or the core envelope space.

Referring to FIGS. 13, 14A-14E, and 15A-15B, an absorbent core 40 may be disposed between a topsheet 30 and a backsheet 49, which may be formed of one or more of materials such as outer backsheet nonwoven layer 52 and liquid-impermeable polymer film layer 50. These materials may be seamed together to form a longitudinal seam 27, and thereby form an envelope space that contains absorbent core 40. It can be seen that formation of a seam 27 may consume portions of materials 49, 30 at the longitudinal edges of the chassis 10. Thus, a seam such as seam 27 is formed at the expense of adding extra materials 49, 30 to provide material for the seam; taking lateral waist circumference away from that available to be taken up by the stretch panel; and/or taking lateral waist circumference away from that available to be taken up by the core envelope space.

Additionally, most disposable diapers and training pant products currently in the market have a system of cuffs designed to provide a gasketing function about the wearer's legs and crotch areas, for better containment of exudates. In the crotch region and waist regions proximate the crotch region, material forming such cuffs often also must be joined to the chassis by a seam structure, which can consume its own share of materials and lateral circumference.

Rather than providing separate seams for cuffs, to preserve lateral circumference available for the core envelope and/or side panels, it may be desirable to combine the seam structures joining the side panels to the chassis, joining the topsheet to the backsheet, and joining the cuffs to the chassis.

Figure 13:
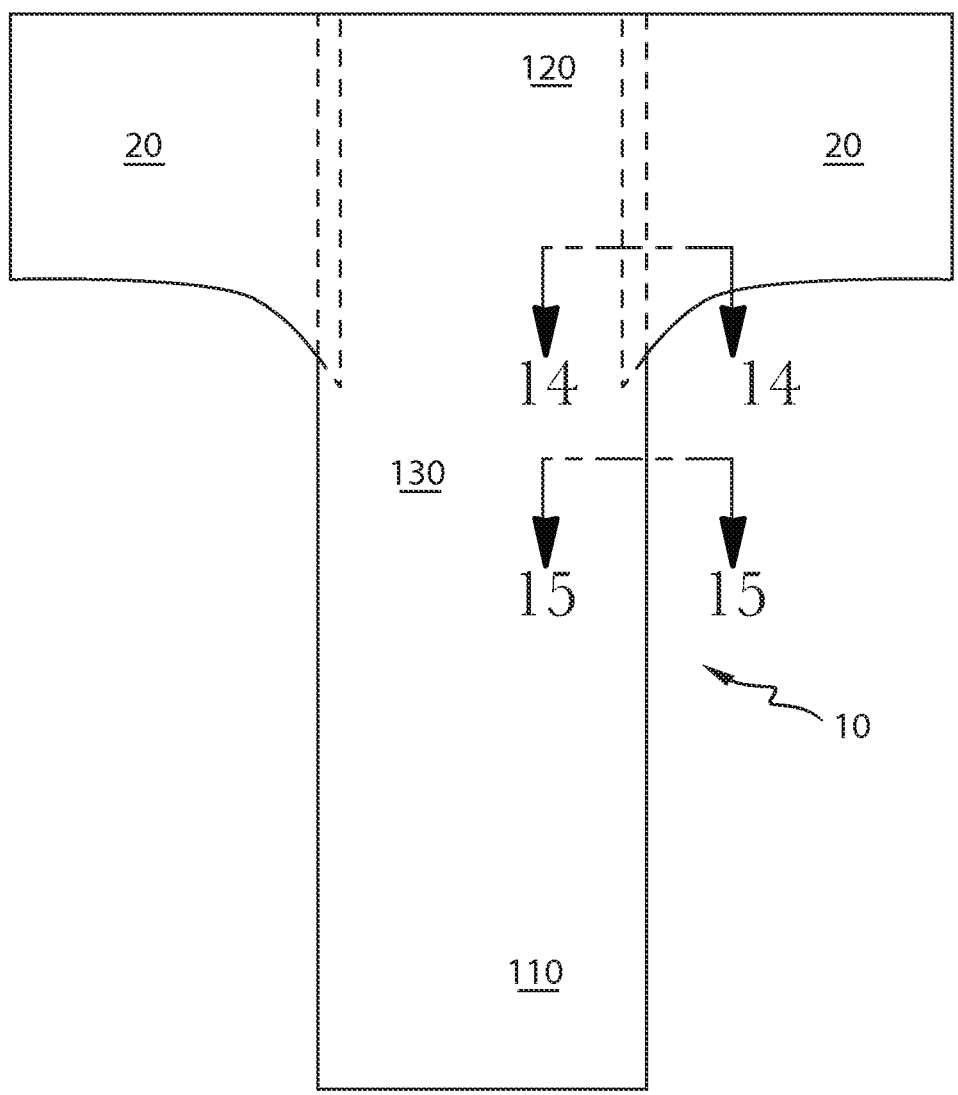
FIG. 13 is a schematic plan view of a precursor structure of a pant including a chassis and side panels, depicted schematically as it would appear with the chassis stretched out to its fiillest lateral and longitudinal extents against any contraction caused by elastic members in the chassis, laid out flat, garment-facing side up.
Figure 14A:
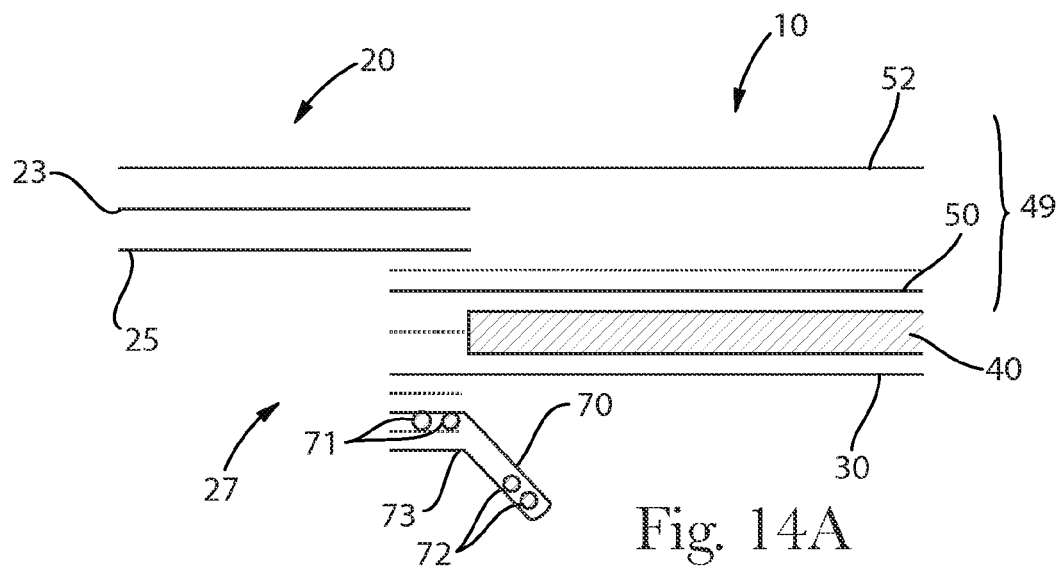
FIG. 14A is a schematic, exploded, lateral cross-sectional view of a seam having a sandwiched configuration, and portions of a chassis and side panel at the seam arranged in one configuration, and also depicting a barrier cuff in one configuration attached at the seam, longitudinally below a location at which such cuff would be have its free edge tacked/bonded down.
Figure 14B:
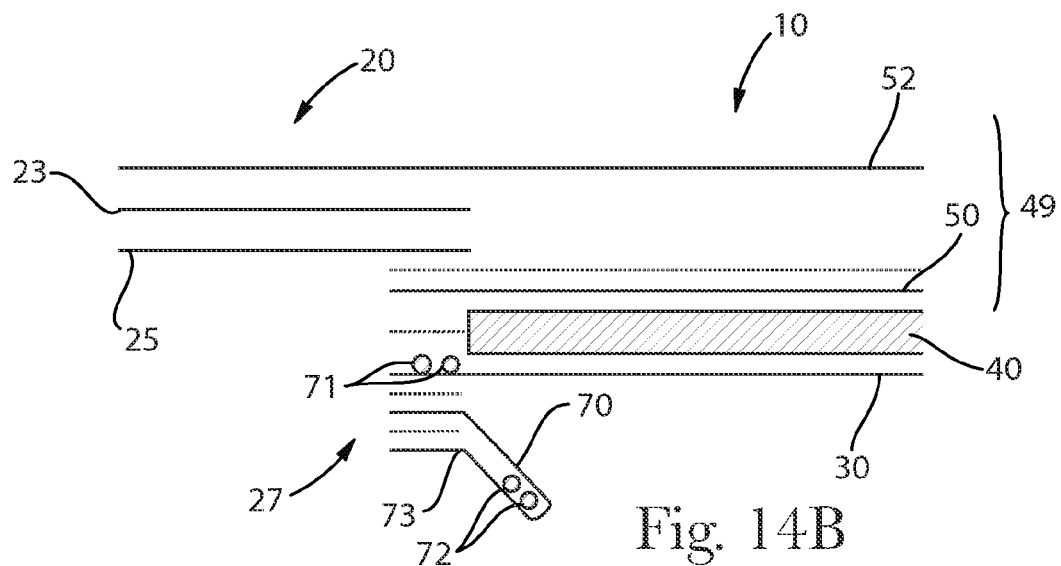
FIG. 14B is a schematic, exploded, lateral cross-sectional view of a seam having a sandwiched configuration, and portions of a chassis and side panel at the seam arranged in one configuration, and also depicting a barrier cuff in an alternative configuration attached at the seam, longitudinally below a location at which such cuff would be have its free edge tacked/bonded down.
Figure 14E:
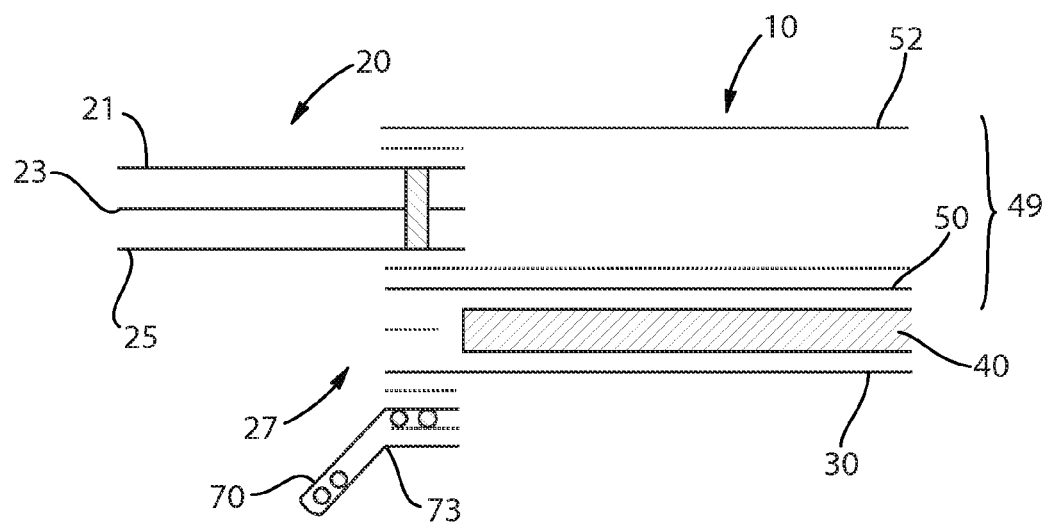
FIG. 14E is a schematic, exploded, lateral cross-sectional view of a seam having a sandwiched configuration, and portions of a chassis and side panel at the seam arranged in an alternative configuration, and also depicting a barrier cuff in another alternative configuration attached at the seam, longitudinally below a location at which such cuff would be have its free edge tacked/bonded down.
Figure 15A:
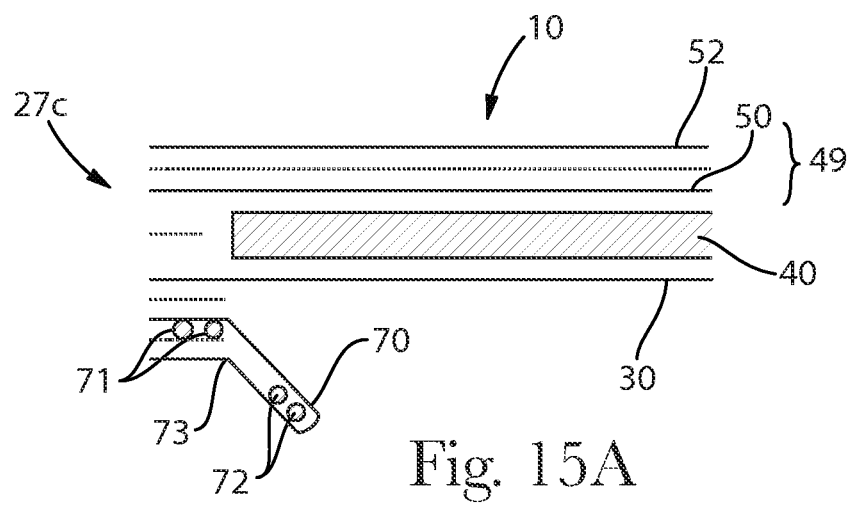
FIG. 15A is a schematic, exploded, lateral cross-sectional view of a combination seam joining portions of a chassis and side a barrier cuff in one configuration attached at the seam in the crotch region.
Figure 15B:
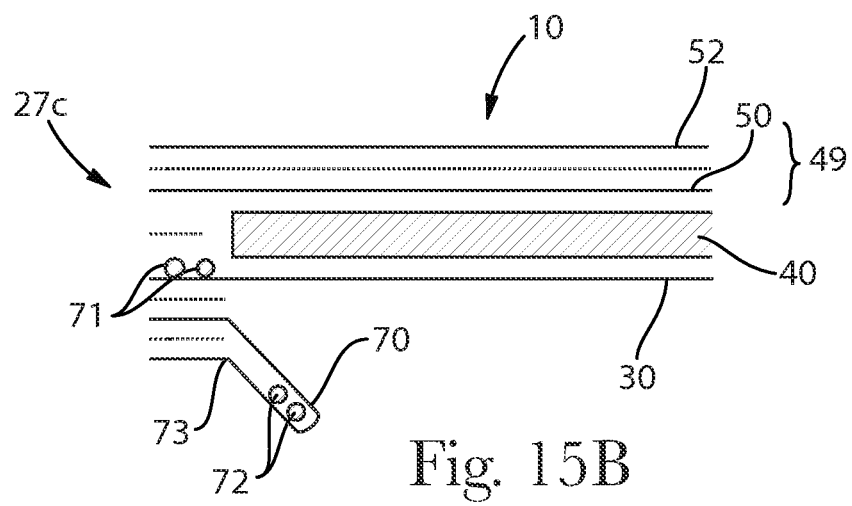
FIG. 15B is a schematic, exploded, lateral cross-sectional view of a combination seam joining portions of a chassis and side a barrier cuff in an alternative configuration attached at the seam in the crotch region.

Referring to FIG. 13, a precursor structure to a pant may include a chassis 10 with side panels 20. The seam joining the side panels 20 to the chassis 10 may have a cross section such as schematically depicted in FIGS. 14A-14E. FIGS. 14A and 14B depict a sandwiched seam construction joining side panel 20 to chassis 10 similar to that depicted in FIG. 10. FIG. 14C depicts an overlapped seam construction joining side panel 20 to chassis 10 similar to that depicted in FIG. 7A. FIGS. 14D and 14E depict a sandwiched seam construction joining side panel 20 to chassis 10 similar to that depicted in FIG. 8A. It can be seen in these figures that barrier cuff 70 may be joined to the inside of the chassis along the same seam 27 as joins side panel 20 to chassis 10. Material forming barrier cuff 70 may be joined to topsheet 30 along seam 27 by adhesive as suggested in, e.g., FIGS. 14A, 14B, or may be joined along seam 27 by mechanical bonds 60 that bond some or all of the overlying/stacked layers, as suggested in, e.g., FIG. 14C. In order to minimize the lateral waist circumference that is consumed by longitudinal seams, the material forming barrier cuff 70 may overlay and/or be stacked with other materials joined at seam 27, such that seam 27 includes all layers 52, 50, 30 and materials forming cuff 70, and commonly joins all such layers along the same seam 27.

Barrier cuff 70 may be formed of a single layer of material (e.g., a nonwoven) folded over on itself as suggested in the figures. It may include one or more longitudinal strands of pre-tensioned elastomeric material (such as LYCRA spandex) to form leg edge elastic members 71 and inner edge elastic members 72. Pre-tensioned inner edge elastic members 72 create longitudinal tension forces along the inner edge of barrier cuff 70, causing it to tend to stand up and conform to the wearer's anatomy when the pant is worn, providing a gasketing function that helps contain exudates. Pre-tensioned leg edge elastic members 71 cause the leg openings to gather around the wearer's legs when the pant is worn, providing for better appearance and fit of the pant, and providing a secondary guard against leakage of exudates. As may be appreciated by comparing FIGS. 14A and 1413, and 15A and 15B, leg edge elastic members 71 may be positioned within the folded layer of material forming barrier cuff 70, or may be positioned between topsheet 30 and backsheet 49. Alternatively, leg edge elastic members 71 may be positioned between topsheet 30 and the material forming barrier cuff 70. Cuff 70 may extend from a fold 73 that is oriented laterally inwardly relative the chassis (as depicted in FIGS. 14A-14D and 15A-15B), or may extend from a fold 73 that is oriented laterally outwardly relative the chassis (as depicted in FIG. 14E). The cuff 70 configuration and manner of joining at seam 27 described has the advantages of ease of manufacture and minimizing the amount of lateral waist circumference of the pant that is consumed by longitudinal seams.

Complementary Cut Side Panels

It may be desirable to configure side panels such that the lower edges thereof (relative a wearer) are lower at the rear than in the front. This provides for more comfortable fit with greater skin coverage about the wearer's lower outside buttock regions. Thus, referring to FIG. 1, if second waist region 120 of chassis 10 is the rear waist region, it may be desirable that side panels 20 have bottom edges 28a cut such that they extend further down along the waist region at the rear, as suggested by FIG. 1.

However, cutting side panels 20 from stretch laminate stock in a manner similar to that suggested in FIG. 1 may result in the wasting of stretch laminate material and resulting complications during manufacturing, because all of the material removed to create the concave cuts at bottom ends 28a as shown in FIG. 1 may not be recoverable or usable in the manufacturing process. Generally, handling and disposing of cut-off waste in the manufacturing process at ordinary rates of production of such articles presents a set of problems which must be addressed; thus, it is desirable to avoid cut-off waste where possible.

Figure 11:
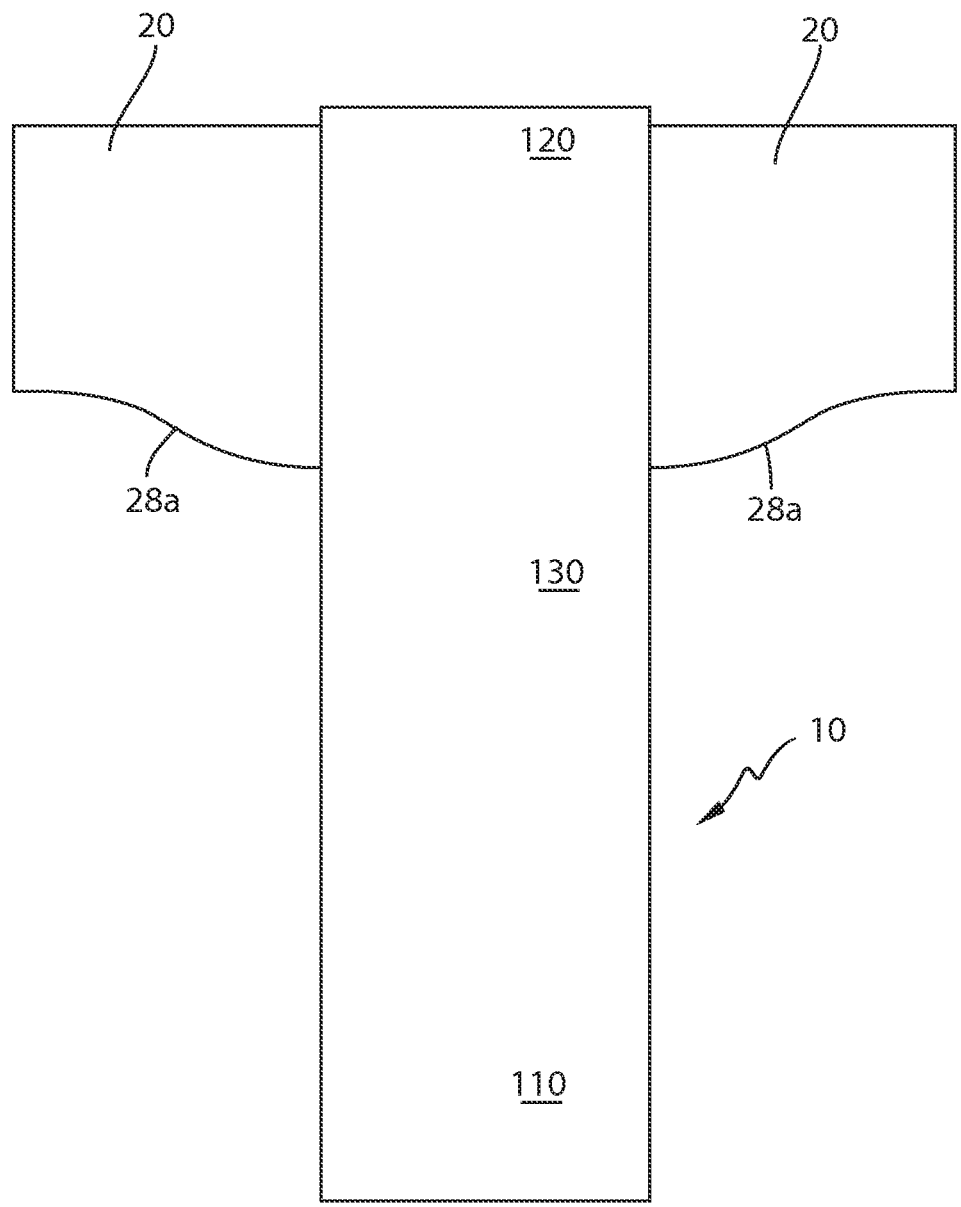
FIG. 11 is a schematic plan view of a precursor structure of a pant including a chassis and side panels, depicted schematically as it would appear with the chassis stretched out to its fullest lateral and longitudinal extents against any contraction caused by elastic members in the chassis, laid out flat, garment-facing side up, having side panels with curved-cut edges having reverse symmetry about inflection points.

It may be possible to eliminate such potential waste by configuring the bottom edge cuts of stretch panels 20 differently. FIG. 11 depicts an alternative bottom edge cut design for side panels 20. If second waist region 120 is the rear waist region, the bottom edges 28a of side panels 20 still extend further down along the waist region at the rear, providing the fit and skin coverage benefits noted above. Further however, bottom edge 28a cuts as depicted in FIG. 11 may eliminate wasted stretch laminate material as a result of the shape of the cuts.

Figure 12:
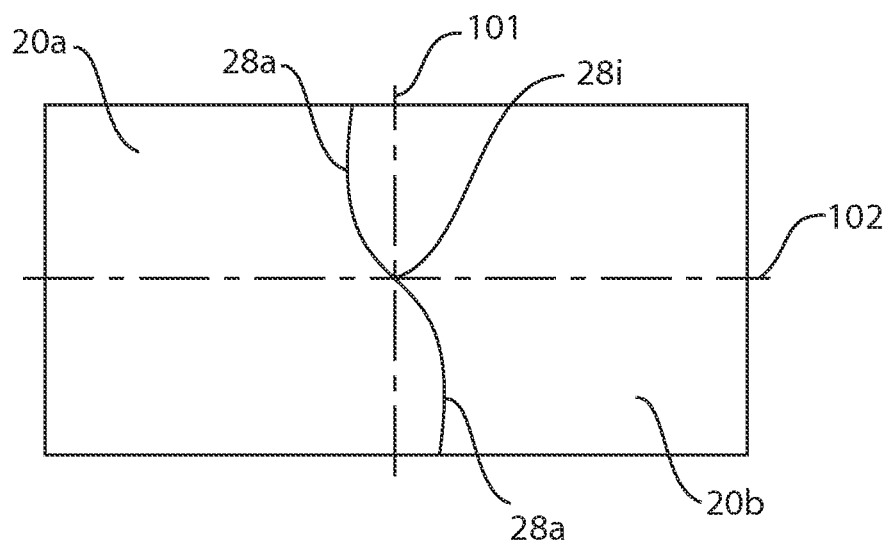
FIG. 12 is a schematic plan view of a portion of stretch laminate material cut to form precursors of two side panels.

It will be appreciated that the each of the bottom edge 28a cuts depicted in FIG. 11 may be characterized by having an inflection point about which curves on either side of the inflection point are negatively symmetrical. FIG. 12 illustrates this characteristic more clearly. FIG. 12 is a schematic plan view of a rectangular portion of stretch laminate material having perpendicular first and second axes 101, 102, and a cut to form precursors of two side panels 20a, 20b. The cut forms the bottom edges 28a of the two respective side panel precursors 20a, 20b. The cut has an inflection point 28i at the intersection of axes 101, 102. The cut is negatively symmetrical about the inflection point 28i. Thus, bottom edges 28a of two side panel precursors can be formed by a single cut, with no material wasted along the cut. It will be appreciated that, following such cut, bottom edges 28i of two side panels 20 have identical profiles.

Test Methods

Elongation and Set Test

A commercial tensile tester (e.g., from Instron Engineering Corp. (Canton, Mass.) or SINTECH-MTS Systems Corporation (Eden Prairie, Minn.)) is used for this test. The instrument is interfaced with a computer for controlling the test speed and other test parameters, and for collecting, calculating and reporting the data. Elongation and set are measured under typical laboratory conditions (i.e., room temperature of 20° C. and relative humidity of 50%).

A rectangular sample 4.00 cm long of the subject laminate material is taken, with sample length for this test measured in the lateral direction relative the pant from which the sample is taken. The rectangular sample is cut 4.00 cm long (lateral direction) by 3.00 cm wide (longitudinal direction).

Procedure

1. Select appropriate clamps and a load cell for the test. The jaws of the respective clamps must have straight edges and be wide enough along such edges to grasp the entire width of the sample (e.g., at least 3.00 cm wide), and clamp substantially along a plane through the tester's line of pull. The load cell is selected so that the tensile response from the sample tested will be between 25% and 75% of the capacity of the load cells or the load range used. A 50-100 N load cell is typical.

2. Calibrate the tester according to the manufacturer's instructions.
3. Set the gauge length at 20.0 mm.
4. Place the sample in the respective clamps such that the longer edges of the sample (i.e., along the 4.00 cm length) are substantially parallel to the gauge length direction (perpendicular the clamp jaw edges), with 1.00 cm of the sample at each end in one of the clamps; and clamp the respective jaws about the sample.
5. Perform the elongation and set test with the following steps:
    a. First cycle loading: Pull the sample to 50% elongation (i.e., distance between respective jaws extended to 30.0 mm) at a constant cross head speed of 250 mm/min.
    b. First cycle unloading: Hold the sample at 50% elongation for 30 seconds and then return the crosshead to its starting position at a constant cross head speed of 250 mm/min. The sample is held in the unloaded state for 1 minute prior to measuring the first cycle % set.
    c. Second cycle loading: Pull the sample to 50% elongation (relative its original length—i.e., distance between jaws again extended to 30.0 mm) at a constant cross head speed of 250 mm/min.
    d. Second cycle unloading: Hold the sample at 50% elongation for 30 seconds and then return crosshead to its starting position at a constant cross head speed of 250 mm/min.

A computer data system records the force exerted on the sample during the loading and unloading cycles. From the resulting time-series (or, equivalently, distance-series) data generated, the % set can be calculated. The % set is the increase in unloaded length after the first loading/unloading cycle, divided by the initial pre-load length×100%. The increase in unloaded length after the first loading/unloading cycle is approximated by the length measured in the second loading cycle at a tensile force of 0.10 N. (The nominal 0.10 N force is selected to be sufficiently high to remove the slack in a sample that has experienced some permanent plastic deformation in a loading cycle, but low enough to impart, at most, insubstantial stretch to the sample.)

The Elongation and Set Test can be suitably modified depending on the expected attributes and/or properties of the particular material sample to be measured. For example, the Test can be suitably modified where a sample of the length and width specified above are not available from the subject pant.

Color Measurement; Determination of ΔE*

Color measurements are made using a tristimulus color meter (spectrophotometer/colorimeter) such as a HunterLab Labscan XE operated under Universal Software 4.1 (available from Hunter Associates Laboratory Inc., Reston Va.) or equivalent.

Configure the instrument as follows:

| | |
|---|---|
| Color Scale | CIE L*a*b* |
| Illumination | C |
| Standard Observer | 2° |
| Geometry | 45/0° |
| Port Diameter | 0.7 inch |
| Viewing Area Diameter | 0.5 inch |
| UV Filter | Nominal |

Calibrate the instrument according to the vendor instructions using the standard black and white tiles provided by the vendor. Calibration should be performed each day before analyses are performed.

Procedure

Obtain each specimen of a backsheet from a pant by separating away a portion of the backsheet along the location where it meets the side panel, including the polymer film layer together with the outer backsheet nonwoven layer. Use a freeze spray as necessary to deactivate or reduce effectiveness of any adhesives, so as to enable separation of the portion. Identify a section that is undamaged by the separating step. From that section, cut a square specimen 2.5 cm×2.5 cm.

Obtain each specimen of a side panel by cutting a square section 2.5 cm×2.5 cm from a side panel, including the component layers forming the side panel, but not including any other layers that may be present at or near the seam where the side panel joins the chassis.

To measure each specimen, place the specimen flat on the instrument with the outer (garment-facing) surface facing the colorimeter's measurement port. Place the white standard tile on the other surface of the specimen, centered over the instrument port for use as a uniform backing. Take readings for L* a* b* values and record to 0.01 units.

Calculations and Reporting

Differences between the paired measurements are calculated using the following standard equation:

$$\Delta E^* = [(L^*_1 - L^*_2)^2 + (a^*_1 - a^*_2)^2 + (b^*_3 - b^*_2)^2]^{0.5},$$

where $L^*_1$, $a^*_1$ and $b^*_1$ are averages of values measured for backsheet specimens, and $L^*_2$, $a^*_2$ and $b^*_2$ are averages of values measured for side panel specimens.

The respective L*, a* and b* values are measured for at least 3 pairs of replicate specimens (3 pairs of respective backsheet and side panel specimens), and averaged. ΔE* is calculated from the respective averaged values, and reported to 0.1 units.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

Embodiments of pants having any of various combinations of the features described above may be constructed, for purposes of incorporating the benefits of those features as described. While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent pant, comprising:
a chassis section having a front waist region, a rear waist region, a crotch region between the front waist region and the rear waist region, a longitudinal center line, a lateral center line, a topsheet, a backsheet and an absorbent core disposed between the topsheet and the backsheet, the backsheet comprising an inner layer of liquid-impermeable polymer film and an outer backsheet nonwoven layer, the layer of liquid-impermeable polymer film and outer backsheet nonwoven layer each having a pair of lateral waist edges and a pair of longitudinal edges; and a pair of side panels joining the front waist region to the rear waist region, each of the side panels being formed of a stretch laminate material comprising an elastic member laminated between first and second layers of side panel nonwoven, each side panel comprising a single section of the stretch laminate material joining the front waist region at a front seam and joining the rear waist region at a rear seam;

wherein one of the front seam or the rear seam is of overlapping configuration wherein each of the first and second layers of side panel nonwoven overlies the outer backsheet nonwoven layer on the outside thereof, and the one of the front seam or the rear seam of overlapping configuration comprises a plurality of mechanical bond sites bonding the stretch laminate material to at least the backsheet;

wherein the other of the front seam or the rear seam is of sandwiched configuration wherein the side panel is directly bonded to the inner layer of liquid-impermeable polymer film at a direct bond location; and wherein the side panel at the front seam or the rear seam of sandwiched configuration has an Active Width, and the direct bond location is laterally inset from a longitudinal edge of the outer backsheet nonwoven layer by a distance that is at least 10% to 50% of the Active Width.

2. An absorbent pant according to claim 1 wherein the elastic member is a film having a front edge and a rear edge.

3. An absorbent pant according to claim 2 wherein the front edge or the rear edge of the elastic film proximate the seam having the sandwiched configuration is disposed laterally outward of the deposit of adhesive.

4. An absorbent pant according to claim 1 wherein each of the first and second layers of side panel nonwoven is disposed between the inner layer of liquid-impermeable polymer film and the outer backsheet nonwoven layer, along the other of the front seam or the rear seam of sandwiched configuration.

5. An absorbent pant according to claim 4 wherein at the seam of sandwiched configuration the layer of elastic film is also disposed between the inner layer of liquid-impermeable polymer film and the outer backsheet nonwoven layer.

6. An absorbent pant according to claim 1 wherein the front seam is of overlapping configuration, and the rear seam is of sandwiched configuration.

7. An absorbent pant according to claim 6 wherein either the front waist region, the rear waist region or both do not have lateral elastic members thereacross and proximate to edges thereof.

8. An absorbent pant according to claim 1 wherein at least a portion of the plurality of mechanical bond sites are discrete from one another such that unbonded areas lie between them.

9. An absorbent pant according to claim 8 wherein each of the plurality of mechanical bond sites has an elongate shape with its longest dimension measurable along a direction that is inclined as it moves laterally away from the longitudinal center line.

10. An absorbent pant according to claim 1 wherein a tophat configuration is formed by intersections between the backsheet and the side panels.

11. An absorbent pant according to claim 1 wherein the side panels are tinted to provide a visual contrast with materials of the chassis, thereby creating an indicium of a location of the front seam or rear seam having the overlapping configuration.

12. An absorbent pant according to claim 1 wherein the stretch laminate material comprises a deposit of adhesive between one of the first and second layers of side panel nonwoven and the layer of elastic film, and the stretch laminate material is substantially free of a deposit of adhesive between the other of the first and second layers of side panel nonwoven and the layer of elastic film.

13. An absorbent pant according to claim 1 further comprising a barrier cuff formed of material joined to and overlapping materials joined at the front seam and at the rear seam.

14. An absorbent pant according to claim 1 wherein the side panel is adhesively bonded to the inner layer of liquid-impermeable polymer film by a deposit of adhesive.

15. An absorbent pant according to claim 1 wherein at the one of the front seam or the rear seam of overlapping configuration, the side panel is separably and refastenably attached to the chassis section via a fastener component affixed directly to the side panel or the chassis section.

16. An absorbent pant, comprising:
- a chassis section having a front waist region, a rear waist region, a crotch region between the front waist region and the rear waist region, a longitudinal center line, a lateral center line, a topsheet, a backsheet and an absorbent core disposed between the topsheet and the backsheet, the backsheet comprising an inner layer of liquid-impermeable polymer film and an outer backsheet nonwoven layer, the layer of liquid-impermeable polymer film and outer backsheet nonwoven layer each having a pair of lateral waist edges and a pair of longitudinal edges; and
- a pair of side panels joining the front waist region to the rear waist region, each of the side panels being formed of a stretch laminate material comprising an elastic member laminated between first and second layers of side panel nonwoven, each side panel comprising a single section of the stretch laminate material joining the front waist region at a front seam and joining the rear waist region at a rear seam;
- wherein one of the front seam or the rear seam is of overlapping configuration wherein each of the first and second layers of side panel nonwoven overlies or underlies the chassis to the outside or inside thereof, and the one of the front seam or the rear seam comprises a plurality of mechanical bond sites bonding the stretch laminate material to at least the backsheet;
- wherein the other of the front seam or the rear seam is of sandwiched configuration wherein the side panel is directly bonded to the inner layer of liquid-impermeable polymer film at a direct bond location; and
- wherein the side panel at the front seam or the rear seam of sandwiched configuration has an Active Width, and the direct bond location is laterally inset from a longitudinal edge of the outer backsheet nonwoven layer by a distance that is at least 10% to 50% of the Active Width.

\* \* \* \* \*